United States Patent [19]

Russell

[11] Patent Number: 5,710,169

[45] Date of Patent: Jan. 20, 1998

[54] THERAPEUTIC HETEROCYCLES

[75] Inventor: Keith Russell, Newark, Del.

[73] Assignee: Zeneca Limited, London, United Kingdom

[21] Appl. No.: 547,512

[22] Filed: Oct. 24, 1995

[30] Foreign Application Priority Data

Oct. 25, 1994 [GB] United Kingdom .................. 9421411
Jun. 17, 1995 [GB] United Kingdom .................. 9512367

[51] Int. Cl.$^6$ .................. A61K 31/445; C07D 211/52
[52] U.S. Cl. .................. 514/327; 514/252; 514/262; 514/291; 514/297; 514/316; 514/318; 514/320; 514/322; 514/323; 514/326; 514/331; 544/310; 544/405; 546/90; 546/102; 546/188; 546/189; 546/194; 546/196; 546/199; 546/200; 546/201; 546/207; 546/208; 546/210; 546/211; 546/213; 546/214; 546/217; 546/234
[58] Field of Search .................. 544/240, 333, 544/336, 310, 405; 546/80, 104, 189, 194, 199, 198, 201, 202, 208, 209, 210, 212, 214, 90, 102, 188, 196, 200, 207, 211, 213, 217, 237; 514/252, 262, 291, 297, 316, 318, 320, 322, 323, 326, 327, 331

[56] References Cited

U.S. PATENT DOCUMENTS

| | | | |
|---|---|---|---|
| 3,518,274 | 6/1970 | Strycker | 546/234 |
| 3,862,946 | 1/1975 | Havers | 546/234 |
| 3,906,100 | 9/1975 | Havera | 514/331 |
| 4,782,061 | 11/1988 | Kruse et al. | 514/254 |
| 4,962,113 | 10/1990 | Tsushima et al. | 514/307 |
| 5,236,921 | 8/1993 | Emonds-Alt et al. | 514/252 |

FOREIGN PATENT DOCUMENTS

| | | |
|---|---|---|
| 2029275 | 5/1991 | Canada . |
| 2067924 | 11/1992 | Canada . |
| 2090785 | 9/1993 | Canada . |
| 0190472 | 8/1986 | European Pat. Off. . |
| 0428434 | 5/1991 | European Pat. Off. . |
| 0474561 | 3/1992 | European Pat. Off. . |
| 0512901 | 11/1992 | European Pat. Off. . |
| 0512902 | 11/1992 | European Pat. Off. . |
| 0515240 | 11/1992 | European Pat. Off. . |
| 0559538 | 9/1993 | European Pat. Off. . |
| 0625509 | 11/1994 | European Pat. Off. . |
| 0630887 | 12/1994 | European Pat. Off. . |
| 0680962 | 11/1995 | European Pat. Off. . |
| 923177 | of 0000 | South Africa . |
| 923178 | 1/1993 | South Africa . |
| 2248449 | 4/1992 | United Kingdom . |
| WO 88/02362 | 4/1988 | WIPO . |
| WO 91/09844 | 7/1991 | WIPO . |
| WO 93/10073 | 5/1993 | WIPO . |
| WO 93/22279 | 11/1993 | WIPO . |
| WO 94/10146 | 5/1994 | WIPO . |
| WO 94/29309 | 12/1994 | WIPO . |
| WO 95/05377 | 2/1995 | WIPO . |
| WO 95/12577 | 5/1995 | WIPO . |
| WO 95/15961 | 6/1995 | WIPO . |
| WO 95/16682 | 6/1995 | WIPO . |

OTHER PUBLICATIONS

Maggi, C.A. et al, American Review of Respiratory Disease, 1991(Aug.), 144(2), pp. 363–367, abstract only.

A. Graham et al., "Isolation and Characterization of the Human Lung NK–2 Receptor Gene Using Rapid Amplification of cDNA Ends", *Biochemical and Biophysical Research Communications*, (1991), vol. 177, No. 1, 0–16.

X. Emonds-Alt et al., "Pharmacological Profile and Chemical Synthesis of SR 48968, a Non-Peptide Antagonist of the Neurokinin A (NK2) Receptor", *Biorganic & Medicinal Chemistry Letters*, (1993), vol. 3, No. 5, 925–930.

D. Anarony et al., "Pharmacologic Characterization of the Novel Ligand [4,5-3H-LEUS]Neurokinin-A Binding to NK–2 Receptors on Hamster Urinary Bladder Membranec", *Neuropeptidec*, (1992), 23, 121–130.

M. Needham et al., "LCR/MEL: A Versatile System for High-Level Expression of Heterologous Proteins in Erythroid Cells", *Nucleic Acids Research*, (1992), vol. 20, No. 5, 997–1003.

O. E. Fancher et al., "New Analgesic N-Substituted Carboxamides", *Analgenic N-Substituted Carboxomides*, (1964), 721–725.

*Primary Examiner*—C. Warren Ivy
*Assistant Examiner*—Garth M. Dahlen
*Attorney, Agent, or Firm*—Robert J. Harris; Paul R. Darkes

[57] ABSTRACT

Compounds of formula I

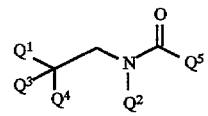

wherein $Q^1$, $Q^2$, $Q^3$, $Q^4$, and $Q^5$ have any of the meanings given in the specification, their N-oxides, and their pharmaceutically acceptable salts are nonpeptide antagonists of SP and NKA are useful for the treatment of asthma, etc. Also disclosed are pharmaceutical compositions, processes for preparing the compounds of formula I and intermediates.

5 Claims, No Drawings

THERAPEUTIC HETEROCYCLES

This invention concerns novel substituted 1,2-ethanediamine derivatives which antagonize the pharmacological actions of the endogenous neuropeptide tachykinins known as neurokinins, particularly at the neurokinin 1 (NK1) and the neurokinin 2 (NK2) receptors. The novel 1,2-ethanediamine derivatives are useful whenever such antagonism is desired. Thus, such compounds may be of value in the treatment of those diseases in which the NK1 and/or NK2 receptor is implicated, for example, in the treatment of asthma and related conditions. The invention also provides pharmaceutical compositions containing the novel 1,2-ethanediamine derivatives for use in such treatment, methods for their use, and processes and intermediates for the manufacture of the novel 1,2-ethanediamine derivatives.

The mammalian neurokinins comprise a class of peptide neurotransmitters which are found in the peripheral and central nervous systems. The three principal neurokinins are SP (SP), Neurokinin A (NKA) and Neurokinin B (NKB). There are also N-terminally extended forms of at least NKA. At least three receptor types are known for the three principal neurokinins. Based upon their relative selectivities favoring the neurokinin agonists SP, NKA and NKB, the receptors are classifed as neurokinin 1 (NK1), neurokinin 2 (NK2) and neurokinin 3 (NK3) receptors, respectively. In the periphery, SP and NKA are localized in C-afferent sensory neurons, which neurons are characterized by non-myelinated nerve endings known as C-fibers, and are released by selective depolarization of these neurons, or selective stimulation of the C-fibers. C-Fibers are located in the airway epithelium, and the tachykinins are known to cause profound effects which clearly parallel many of the symptoms observed in asthmatics. The effects of release or introduction of tachykinins in mammalian airways include bronchoconstriction, increased microvascular permeability, vasodilation, increased mucas secretion, neurogenic inflamation and activation of mast cells. Thus, the tachykinins are implicated in the pathophysiology and airway hyperresponsiveness observed in asthmatics; and blockade of the action of released tachykinins may be useful in the treatment of asthma and related conditions. A cyclopeptide antagonists (FK-224) selective for both NK1 and NK2 receptors has demonstrated clinical efficacy in human patients suffering from asthma and chronic bronchitis. M. Ichinose, et al., *Lancet*, 1992, 340, 1248. Nonpeptidic tachykinin antagonists have been reported, for example in European Patent Application, Publication Number (EPA) 428434, EPA 474561, EPA 512901, EPA 512902, EPA 515240 and EPA 559538, as well as in WO 94/10146.

K. Nagarajan, et al., *Proc. Indian Acad. Sci.* (*Chem. Sci.*), 1992, 104, 383–397 (Nagarajan), discloses the synthesis of 1,2-ethanediamine derivatives of formula I (formula set out hereinbelow following the Examples, together with other formulae denoted by Roman numerals) wherein $Q^1$ is a pyrrolidino or piperidino radical of formula Id and $Q^4$ is phenyl, 3,4-dimethoxyphenyl, 3,4-(methylenedioxy)phenyl, 3-methoxyphenyl, or 2-thienyl. The compounds disclosed in Nagarajan have been excluded from the definition of the compounds of the invention hereinbelow. Nagarajan does not disclose pharmaceutical compositions containing the compounds disclosed therein, nor does Nagarajan disclose a pharmaceutical utility for the compounds.

We have discovered a series of non-peptidic antagonists of the NK1 and NK2 receptors, and this is the basis for our invention.

According to the invention, there is provided a Compound of the invention which is a compound of formula I, wherein $Q^1$ is a radical selected from the group of radicals of formulae Ia, Ib, Ic, Id, Ie, If, Ig, Ih, Ij, Ik and Im, wherein for a radical of formula Ia, $Z^a$ is nitrogen or a group $CR^{ad}$ in which $R^{ad}$ is hydrogen or $R^{ac}$ together with $R^{ac}$ and the existing carbon to carbon bond forms a double bond; $R^{aa}$ is Ar or Het; $R^{ab}$ is hydrogen and $R^{ac}$ is hydrogen or hydroxy or $R^{ac}$ together with $R^{ad}$ and the existing carbon to carbon bond forms a double bond, or $R^{ac}$ and $R^{ad}$ together form a diradical —(CH$_2$)$_j$— in which j is an integer from 1 to 5; or $R^{ab}$ and $R^{ac}$ together form a diradical —(CH$_2$)$_k$— in which k is an integer from 2 to 6, or $R^{ab}$ and $R^{ac}$ together are oxo or dialkylaminoalkyloxyimino of formula =N—O—(CH$_2$)$_q$—NR$^{ae}$R$^{af}$ in which q is the integer 2 or 3 and $R^{ae}$ and $R^{af}$ are independently hydrogen or (1–4C)alkyl, or the radical NR$^{ae}$R$^{af}$ is pyrrolidino, piperidino or morpholino;

for a radical of formula Ib, $Z^b$ is a substituted imino group $R^{ba}$N or $R^{ba}$CH$_2$N in which $R^{ba}$ is (3–7C)cycloalkyl, Ar or Het; or $Z^b$ is a disubstituted methylene group $R^{bb}$(CH$_2$)$_p$—C—$R^{bc}$ in which $R^{bb}$ is Ar or Het; p is the integer 0 or 1; and $R^{bc}$ is hydrogen, hydroxy, (1–4C)alkoxy, (1–4C)alkanoyloxy, COOR$^{bd}$ (wherein $R^{bd}$ is hydrogen or (1–3C)alkyl), cyano, NR$^{be}$R$^{bf}$ or SR$^{bg}$ in which $R^{be}$ and $R^{bf}$ are independently hydrogen, (1–4C)alkyl, (1–4C)hydroxyalkyl or (1–4C)alkanoyl, or the radical NR$^{be}$R$^{bf}$ is pyrrolidino, piperidino or morpholino; and $R^{bg}$ is hydrogen or (1–4C)alkyl; or $R^{bc}$ forms a double bond with the carbon atom to which it is bonded and with the adjacent carbon atom in the piperidine ring; or $Z^b$ is a disubstituted methylene group $R^{bh}$CR$^{bi}$ which forms a spirocyclic ring wherein $R^{bh}$ is phenyl which is joined by an ortho-substituent diradical $X^b$ to $R^{bi}$ in which the phenyl $R^{bh}$ may bear a further substituent selected from halo, (1–3C)alkyl, (1–3C)alkoxy, hydroxy, (1–3C)alkylthio, (1–3C)alkylsulfinyl and (1–3C)alkylsulfonyl; the diradical $X^b$ is methylene, carbonyl or sulfonyl; and $R^{bi}$ is oxy or imino of formula —NR$^{bj}$— in which $R^{bj}$ is hydrogen or (1–3C)alkyl;

for a radical of formula Ic, $R^{ca}$ is Ar or Het; and $Z^c$ is oxo, thio, sulfinyl, sulfonyl or imino of formula —NR$^{cb}$— in which $R^{cb}$ is (1–3C)alkyl or R$^{cc}$R$^{cd}$N—(CH$_2$)$_q$— in which q is the integer 2 or 3 and in which $R^{cc}$ and $R^{cd}$ are independently hydrogen or (1–3C)alkyl or the radical R$^{cc}$R$^{cd}$N is pyrrolidino, piperidino or morpholino;

for a radical of formula Id, $R^{da}$ is 1, 2 or 3;

for a radical of formula Ie, $J^e$ is oxygen, sulfur or NR$^{ea}$ in which $R^{ea}$ is hydrogen or (1–3C)alkyl; $R^{eb}$ is hydrogen, (1–6C)alkyl which may bear a hydroxy substituent and/or one to three fluoro substituents, (3–6C)alkenyl (in which a vinyl carbon is not bound to nitrogen), 2-hydroxyethyl, (3–7C)cyloalkyl, Ar or Het; $R^{ec}$ is hydrogen, (1–6C)alkyl which may bear a hydroxy substituent and/or one to three fluoro substituents, (3–6C)cycloalkyl, (1–5C)alkoxy (only when $J^e$ is oxygen), (3–6C)cycloalkoxy (only when $J^e$ is oxygen), or an amino group of formula NR$^{ed}$R$^{ee}$ containing zero to seven carbon atoms in which each of $R^{ed}$ and $R^{ee}$ is independently hydrogen, (1–5C)alkyl or (3–6C)cycloalkyl, or the radical NR$^{ed}$R$^{ee}$ is pyrrolidino, piperidino, morpholino, thiomorpholino (or its

3

S-oxide) or piperazinyl (which piperazinyl group may bear a (1–3C)alkyl substituent at the 4-position);

for a radical of formula If, $J^f$ is oxygen, sulfur or $NR^{fa}$ in which $R^{fa}$ is hydrogen or (1–3C)alkyl; $L^f$ is a divalent hydrocarbon group in which the 1-position is bound to the carbon bearing the group $J^f$, the divalent group $L^f$ being selected from trimethylene, cis-propenylene, tetramethylene, cis-butenylene, cis-but-3-enylene, cis,cis-butadienylene, pentamethylene and cis-pentenylene which divalent group $L^f$ itself may bear one or two methyl substituents;

for a radical of formula Ig, $Z^g$ is (1–8C)alkyl or (3–8C)cycloalkyl which may bear one or more substituents selected from the group consisting of halo, (3–6C)cycloalkyl, cyano, nitro, hydroxy, (1–4C)alkoxy, (1–5C)alkanoyloxy, aroyl, heteroaroyl, oxo, imino (which may bear a (1–6C)alkyl, (3–6C)cycloalkyl, (1–5C)alkanoyl or aroyl substituent), hydroxyimino (which hydroxyimino may bear a (1–4C)alkyl or a phenyl substituent on the oxygen), an amino group of formula $NR^{ga}R^{gb}$, an amino group of formula $NR^{gc}R^{gd}$, an amidino group of formula $C(=NR^{gg})NR^{ge}R^{gf}$, and a carbamoyl group of formula $CON(OR^{gh})R^{gi}$, but excluding any radical wherein a hydroxy and an oxo substituent together form a carboxy group, wherein an amino group of formula $NR^{ga}R^{gb}$ contains zero to seven carbon atoms and each of $R^{ga}$ and $R^{gb}$ is independently hydrogen, (1–5C)alkyl or (3–6C)cycloalkyl, or the radical $NR^{ga}R^{gb}$ is pyrrolidino, piperidino, morpholino, thiomorpholino (or its S-oxide) or piperazinyl (which piperazinyl may bear a (1–3C)alkyl substituent group at the 4-position); and wherein $R^{gc}$ is hydrogen or (1–3C)alkyl and $R^{gd}$ is (1–5C)alkanoyl, aroyl or heteroaroyl; or $R^{gd}$ is a group of formula $C(=J^g)NR^{ge}R^{gf}$ in which $J^g$ is oxygen, sulfur, $NR^{gg}$ or $CHR^{gj}$; and wherein the amino group $NR^{ge}R^{gf}$ contains zero to seven carbon atoms and each of $R^{ge}$ and $R^{gf}$ is independently hydrogen, (1–5C)alkyl or (3–6C)cycloalkyl, or the radical $NR^{ge}R^{gf}$ is pyrrolidino, piperidino, morpholino, thiomorpholino (or its S-oxide) or piperazinyl (which piperazinyl may bear a (1–3C)alkyl substituent at the 4-position) or $R^{ge}$ is hydrogen or (1–4C)alkyl and $R^{gf}$ together with $R^{gg}$ forms an ethylene or trimethylene group; $R^{gg}$ is hydrogen, (1–4C)alkyl or together with $R^{gf}$ forms an ethylene or trimethylene group; $R^{gj}$ is cyano, nitro or $SO_2R^{gk}$ and $R^{gk}$ is (1–4C)alkyl or phenyl; $R^{gh}$ and $R^{gi}$ are independently (1–3C)alkyl; and in which a cyclic group which is a substituent on $Z^g$ or formed by substitution on $Z^g$ may bear one or more (1–3C)alkyl groups on carbon as further substituents; and in which any aryl or heteroaryl group which is a part of the group $Z^g$ may bear one or more halo, (1–4C)alkyl, (1–4C)alkoxy, cyano, trifluoromethyl or nitro substituents;

for a radical of formula Ih, $G^h$ denotes a single bond, a double bond or a divalent hydrocarbon radical; $J^h$ denotes a radical joined to the ring by a single bond if $G^h$ denotes a double bond or, otherwise, a radical joined by a double bond; $M^h$ denotes a heteroatom, a substituted heteroatom, or a single bond; and $L^h$ denotes a hydrocarbon radical in which the 1-position is attached to $M^h$; wherein the values of $G^h$, $J^h$, $M^h$ and $L^h$ are selected from (a) $G^h$ is a single bond; $J^h$ is oxo or thioxo; $M^h$ is oxy, thio or $NR^{ha}$; and $L^h$ is $L^{ha}$;

(b) $G^h$ is a single bond; $J^h$ is $NR^{hb}$; $M^h$ is $NR^{ha}$; and $L^h$ is $L^{ha}$;

4

(c) $G^h$ is a double bond, $J^h$ is $OR^{ha}$, $SR^{ha}$ or $NR^{hc}R^{hd}$; $M^h$ is nitrogen; and $L^h$ is $L^{ha}$;

(d) $G^h$ is methylene which may bear one or two methyl substituents; $J^h$ is oxo, thioxo or $NR^{he}$; $M^h$ is oxy, thio, sulfinyl, sulfonyl or $NR^{ha}$; and $L^h$ is $L^{hb}$;

(e) $G^h$ is a single bond; $J^h$ is oxo, thioxo or $NR^{he}$; $M^h$ is nitrogen; and $L^h$ is $L^{hc}$;

(f) $G^h$ is methine, which may bear a (1–3C)alkyl substituent; $J^h$ is oxo, thioxo or $NR^{he}$; $M^h$ is nitrogen; and $L^h$ is $L^{hd}$;

(g) $G^h$ is cis-vinylene, which may bear one or two methyl substituents; $J^h$ is oxo, thioxo, or $NR^{he}$; $M^h$ is nitrogen; and $L^h$ is $L^{he}$; and (h) $G^h$ is a single bond; $J^h$ is oxo or thioxo; $M^h$ is a single bond; and $L^h$ is $L^{hf}$; wherein $R^{ha}$ is hydrogen or (1–3C)alkyl; $R^{hb}$ is hydrogen, (1–3C)alkyl, cyano, (1–3C)alkylsulfonyl or nitro; $R^{hc}$ and $R^{hd}$ are independently hydrogen or (1–3C)alkyl or the radical $NR^{hc}R^{hd}$ is pyrrolidino, piperidino, morpholino, thiomorpholino (or its S-oxide) or piperazinyl (which piperazinyl may bear a (1–3C)alkyl substituent at the 4-position); $R^{he}$ is hydrogen or (1–3C)alkyl; $L^{ha}$ is ethylene, cis-vinylene, trimethylene or tetramethylene which radical $L^{ha}$ itself may bear one or two methyl substituents; $L^{hb}$ is ethylene or trimethylene which radical $L^{hb}$ itself may bear one or two methyl substituents; $L^{hc}$ is prop-2-en-1-yliden-3-yl, which radical $L^{hc}$ itself may bear one or two methyl substituents; $L^{hd}$ is cis-vinylene, which radical $L^{hd}$ itself may bear one or two methyl substituents; is $L^{he}$ is methine, which radical $L^{he}$ itself may bear a (1–3C)alkyl substituent; and $L^{hf}$ is 4-oxabutan-1,4-diyl;

for a radical of formula Ij, $X^j$ is (1–6C)alkyl, $—CH_2OR^{ja}$, $—CH_2SR^{ja}$, $—CH_2S(O)R^{jg}$, $—CH_2S(O)_2R^{jg}$, $—COR^{ja}$, $—COOR^{ja}$, $—C(=J^{ja})NR^{jb}R^{jc}$, $—C(R^{ja})(OR^{jd})(OR^{je})$, $—CH_2N(R^{ja})C(=J^{ja})R^{jf}$, $—CH_2N(R^{ja})COOR^{jg}$ or $—CH_2N(R^{ja})C(=J^{ja})NR^{jb}R^{jc}$;

$B^j$ is a direct bond and $L^j$ is a hydrocarbon chain in which the 1-position is bound to $B^j$ and $L^j$ is selected from trimethylene, tetramethylene, cis-1-butenylene and cis,cis-butadienylene; or $B^j$ is $N(R^{jh})$ and $L^j$ is a hydrocarbon chain selected from ethylene, trimethylene and cis-vinylene; or $B^j$ is N and $L^j$ is a hydrocarbon chain in which the 1-position is bound to $B^j$ and $L^j$ is cis,cis-prop-2-en-1-ylidin-3-yl; $J^j$ and $J^{ja}$ are independently oxygen or sulfur; $R^{ja}$, $R^{jf}$ and $R^{jh}$ are independently hydrogen or (1–6C)alkyl; $R^{jb}$ and $R^{jc}$ are independently hydrogen or (1–6C)alkyl; or the radical $NR^{jb}R^{jc}$ is pyrrolidino, piperidino, morpholino, thiomorpholino (or its S-oxide) or piperazinyl (which piperazinyl may bear a (1–3C)alkyl substituent at the 4-position); $R^{jd}$ and $R^{je}$ are independently (1–3C)alkyl or together form a divalent hydrocarbon chain selected from ethylene and trimethylene; $R^{jg}$ is (1–6C)alkyl; and for a radical of formula Ik, $Z^k$ is a nitrogen linked radical of formula LI wherein $E^1$, $E^2$, $E^3$ and $E^4$ form a divalent four membered chain ($—E^1=E^2—E^3=E^4—$) in which each of $E^1$, $E^2$, $E^3$ and $E^4$ is methine; or in which one or two of $E^1$, $E^2$, $E^3$ and $E^4$ is nitrogen and the remaining $E^1$, $E^2$, $E^3$ and $E^4$ are methine; and further wherein one or more of $E^1$, $E^2$, $E^3$ and $E^4$ which is methine may bear a halo, (1–3C)alkyl, hydroxy, (1–3C)alkoxy, (1–3C)alkylthio, (1–3C)alkylsulfinyl or (1–3C)alkylsulfonyl substituent; and wherein the radicals $F^k$, $G^k$, and $I^k(X^k)$ are selected from (a) $G^k$ is a direct bond, $I^k(X^k)$ is a radical having the formula $=C(Z^k)—$ and $F^k$ is a radical selected from $—CH=$ and $—N=$;

(b) $G^k$ is a direct bond, $I^k(X^k)$ is a radical having the formula —C(=J$^k$)— and $F^k$ is a radical selected from —N(R$^{kf}$)—, —CH$_2$—CH$_2$—, —CH=CH—, —CH$_2$—N(R$^{kf}$)— and —CH=N—;

(c) $G^k$ is a radical having the formula —CH$_2$—, $I^k(X^k)$ is a radical having formula —C(=J$^k$)— and $F^k$ is selected from —CH$_2$— and —N(R$^{kf}$)—; and (d) $G^k$ is selected from —CH$_2$—, —CH$_2$—CH$_2$—, —CH=CH— and —N=CH—, $I^k(X^k)$ is a radical having the formula —C(=J$^k$)— and $F^k$ is a direct bond; wherein $J^k$ is oxygen or sulfur; $Z^k$ is —OR$^{ka}$, —SR$^{ka}$, —COR$^{ka}$, —COOR$^{ka}$, —C(=J$^{ka}$)NR$^{kb}$R$^{kc}$ or —C(R$^{ka}$)(OR$^{kd}$)(OR$^{ke}$); $J^{ka}$ is oxygen or sulfur; $R^{ka}$ and $R^{kf}$ are independently hydrogen or (1–6C)alkyl; $R^{kb}$ and $R^{kc}$ are independently hydrogen or (1–6C)alkyl; or the radical NR$^{kb}$R$^{kc}$ is pyrrolidino, piperidino, morpholino, thiomorpholino (or its S-oxide) or piperazinyl (which piperazinyl may bear a (1–3C)alkyl substituent at the 4-position); $R^{kd}$ and $R^{ke}$ are independently (1–3C)alkyl or $R^{kd}$ and $R^{ke}$ together form ethylene or trimethylene; or $Z^k$ is an imido radical selected from phthalimido, succinimido, maleimido, glutarimido, and 3-oxa-, 3-thia- and 3-azaglutarimido, in which the imido radical may bear one or more (1–3C)alkyl substituents and, in addition, the aromatic portion of the phthalimido may bear one or more halo, hydroxy or (1–3C)alkoxy substituents;

for a radical of formula Im, $R^{ma}$ is 1 or 2; and wherein for a radical $Q^1$, Ar is a phenyl radical or an ortho-fused bicyclic carbocyclic radical of nine of ten ring atoms in which at least one ring is aromatic, which radical Ar may be unsubstituted or may bear one or more substituents selected from halo, cyano, trifluoromethyl, (1–4C)alkyl, (1–4C)alkoxy, methylenedioxy, hydroxy, mercapto, —S(O)$_n$R$^{xa}$, (1–5C)alkanoyl, (1–5C)alkanoyloxy, nitro, NR$^{xb}$R$^{xc}$ NR$^{xd}$R$^{xe}$, C(=NR$^{xf}$) NR$^{xg}$R$^{xh}$, CONR$^{xb}$R$^{xc}$ and COOR$^{xj}$ wherein n is the integer 0, 1, or 2; $R^{xa}$ is (1–6C)alkyl, (3–6C)cycloalkyl or phenyl (which phenyl may bear a halo, trifluoromethyl, (1–3C)alkyl or (1–3C)alkoxy substitutent); the radical NR$^{xb}$R$^{xc}$ contains zero to seven carbons and each of $R^{xb}$ and $R^{xc}$ is independently hydrogen, (1–5C)alkyl or (3–6C)cycloalkyl, or the radical NR$^{xb}$R$^{xc}$ is pyrrolidino, piperidino, morpholino, thiomorpholine (or its S-oxide) or piperazinyl (which piperazinyl may bear a (1–3C)alkyl substituent at the 4-position); and wherein $R^{xd}$ is hydrogen or (1–4C)alkyl and $R^{xe}$ is (1–5C)alkanoyl, benzoyl; or a group of formula C(=J$^x$)NR$^{xg}$R$^{xh}$ in which J$^x$ is oxygen, sulfur, NR$^{xf}$ or CHR$^{xi}$; $R^{xf}$ is hydrogen, (1–5C)alkyl or together with $R^{xg}$ forms an ethylene or trimethylene diradical, the radical NR$^{xg}$R$^{xh}$ contains zero to 7 carbons and each of $R^{xg}$ and $R^{xh}$ is independently hydrogen, (1–5C)alkyl or (3–6C)cycloalkyl, or the radical NR$^{xg}$R$^{xh}$ is pyrrolidino, piperidino, morpholino, thiomorpholino (or its S-oxide) or piperazinyl (which piperazinyl may bear a (1–3C)alkyl substituent at the 4-position); or $R^{xg}$ together with $R^{xf}$ forms an ethylene or trimethylene diradical and $R^{xh}$ is hydrogen or (1–5C) alkyl; $R^{xi}$ is cyano, nitro, (1–5C)alkylsulfonyl or phenylsulfonyl; and $R^{xj}$ is hydrogen, (1–5C)alkyl or benzyl; and Het is a radical (or stable N-oxide thereof) attached via a ring carbon of a monocyclic aromatic ring containing five or six ring atoms consisting of carbon and one to four heteroatoms selected from oxygen, sulfur and nitrogen, or an ortho-fused bicyclic heterocycle derived therefrom by fusing a propenylene, trimethylene, tetramethylene or benz-diradical, which radical Het may be unsubstituted or may be substituted on carbon by one or more of the substituents defined above for Ar and may be substituted on nitrogen by (1–3C)alkyl;

$Q^2$ and $Q^3$ are independantly hydrogen or (1–3C)alkyl;

$Q^4$ is phenyl which may bear one or two substituents independently selected from halo, trifluoromethyl, hydroxy, (1–3C)alkoxy, (1–3C)alkyl and methylenedioxy; or $Q^4$ is thienyl, imidazolyl, benzo[b]thiophenyl or naphthyl any of which may bear a halo substituent; or $Q^4$ is biphenylyl; or $Q^4$ is carbon-linked indolyl which may bear a benzyl substituent at the 1-position; and $Q^5$ is formyl, 4-imidazolidinyl, 3-pyrrolidinyl (wherein the nitrogen may optionally be substituted by a substituent selected from (1–3C)alkyl, acyl, and benzyloxycarbonylaminoacetyl), (3–6C)cycloalkyl, trifluoromethyl, 4-piperidino (wherein the nitrogen may optionally be substituted by a substituent selected from (1–3C)alkyl, and acyl), aryl, heteroaryl, pyrid-1-ylmethyl, fluorenyl, β-styryl, a radical of formula XII–XXII or xanthenyl; or $Q^5$ is (1–8C)alkyl which may be substituted by 0–3 substituents selected from aryl, heteroaryl, (aryl)oxy, aryl(1–3C)-alkyl, heteroaryl (1–3C)alkyl, (1–6C)alkyl, (heteroaryl)oxy, benzyloxy, (3–6C)cycloalkyl, adamantyl, norbornanyl, β-styryl, cyano, trifluoromethyl, oxo, hydroxy, (1–4C)alkoxy, —NR$^a$R$^b$, —NC(=O)NR$^c$R$^d$, —NC(=O)OR$^e$, —C(=O)OR$^f$, —S(O)R$^g$, —S(O)$_2$R$^h$, =NR$^i$, SR$^j$, and the radicals of formulae XII–XXII;

$R^a$–$R^b$ are independently selected from hydrogen, acyl, formyl, and (1–4C)alkyl, or the group NR$^a$R$^b$ may form a cyclic group selected from pyrrolidino, piperidino, morpholino, thiomorpholino (or its S-oxide) or piperazinyl (which piperazinyl may bear a (1–3C)alkyl substituent at the 4-position);

$R^c$–$R^f$ and $R^j$ are independently selected from hydrogen, phenyl, benzyl, phenethyl and (1–4C)alkyl;

$R^g$ and $R^h$ are independently selected from hydrogen, phenyl, benzyl, phenethyl, β-styryl and (1–4C)alkyl;

$R^i$ is hydrogen, (1–4C)alkyl, acyl or (1–4C)alkoxy;

wherein any aryl or heteroaryl in, or any aryl or heteroaryl portion of, $Q^5$, or any aryl or heteroaryl portion of $R^a$–$R^j$, may be unsubstituted or may bear 1–5 substituents selected from halo, cyano, trifluoromethyl, (1–4C) alkyl, (1–4C)alkoxy, methylenedioxy, phenoxy, benzyloxy, NR$^l$R$^m$, —NS(O)$_2$aryl (wherein the aryl group may be substituted by 0–3 (1–3C)alkyl groups), hydroxy, —SR$^n$, and nitro; and wherein any β-styryl may optionally be substituted at the β-position by a substituent selected from (1–3C)alkoxy;

wherein $R^k$–$R^m$ are independently selected from hydrogen, acyl, formyl, and (1–4C)alkyl, or the group NR$^k$R$^m$ may form a cyclic group selected from pyrrolidino, piperidino, morpholino, thiomorpholino (or its S-oxide) or piperazinyl (which piperazinyl may bear a (1–3C)alkyl substituent at the 4-position); and $R^n$ is hydrogen or (1–3C)alkyl;

or the N-oxide of a piperidino nitrogen in $Q^1$ indicated by Δ in formulae Ia–Im (or of either basic piperazinyl nitrogen of $Q^1$ when $Z^a$ is nitrogen);

or a pharmaceutically acceptable salt thereof;

or a quaternary ammonium salt thereof in which the piperidino nitrogen in $Q^1$ indicated by $\Delta$ in formulae Ia-Im (or either basic piperazinyl nitrogen of $Q^1$ when $Z^a$ is nitrogen) is a quadricovalent ammonium nitrogen wherein the fourth radical on the nitrogen $R^1$ is (1–4C) alkyl or benzyl and the associated counterion A is a pharmaceutically acceptable anion;

provided that when $Q^1$ is a pyrrolidino or piperidino radical of formula Id, $Q^4$ is not phenyl, 3,4-dimethoxyphenyl, 3,4-(methylenedioxy)phenyl, 3-methoxyphenyl, or 2-thienyl.

A preferred sub-group of compounds of the invention are compounds of formula I as defined above, wherein $Q^5$ is aryl, or heteroaryl; or $Q^5$ is a radical of formula III wherein: a) $R^1$ is aryl, heteroaryl, aryl(1–3C)alkyl or heteroaryl (1–3C)alkyl; and $R^2$ and $R^3$ are independantly hydrogen, aryl, heteroaryl, aryl(1–3C)alkyl, heteroaryl(1–3C)alkyl, (1–6C)alkyl or (3–6C)cycloalkyl; or b) $R^1$ and $R^2$ together with the carbon to which they are attached form a (3–6C) cycloalkyl and $R^3$ is hydrogen or (1–6C)alkyl; wherein any aryl or heteroaryl ring in $Q^5$ may be unsubstituted or may bear one or more substituents selected from halo, cyano, trifluoromethyl, (1–4C)alkyl, (1–4C)alkoxy, methylenedioxy, hydroxy and nitro;

or the N-oxide of a piperidino nitrogen in $Q^1$ indicated by $\Delta$ in formulae Ia-Im (or of either basic piperazinyl nitrogen of $Q^1$ when $Z^a$ is nitrogen);

or a pharmaceutically acceptable salt thereof;

or a quaternary ammonium salt thereof in which the piperidino nitrogen in $Q^1$ indicated by $\Delta$ in formulae Ia-Im (or either basic piperazinyl nitrogen of $Q^1$ when $Z^a$ is nitrogen) is a quadricovalent ammonium nitrogen wherein the fourth radical on the nitrogen $R^1$ is (1–4C) alkyl or benzyl and the associated counterion A is a pharmaceutically acceptable anion.

It will be appreciated that a compound of formula I may contains one or more asymmetically substituted carbon atoms and that such a compound may be isolated in optically active, racemic and/or diastereomeric forms. A compound may exhibit polymorphism. It is to be understood that the present invention encompasses any racemic, optically-active, diastereomeric, polymorphic or stereoisomeric form, or mixture thereof, which form possesses NK1 and NK2 antagonist properties, it being well known in the art how to prepare optically-active forms (for example, by resolution of the racemic form or by synthesis from optically-active starting materials) and how to determine the NK1 and NK2 antagonist properties by the standard tests known in the art and those described hereinafter.

In this specification $R^a$, $R^b$, $R^1$, $R^2$, et cetera stand for generic radicals and have no other significance. It is to be understood that the generic terms "(1–3C)alkyl" and "(1–6C)alkyl" include both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, alkoxy, alkanoyl, et cetera. Halo is fluoro, chloro, bromo or iodo. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five ring atoms consisting of carbon and one to four heteroatoms selected from oxygen, sulfur and nitrogen or containing six ring atoms consisting of carbon and one or two nitrogens, as well as a radical of an ortho-fused bicyclic heterocycle of about eight to ten atoms derived therefrom, particularly a benz-derivative or one derived by fusing a propenylene, trimethylene of tetramethylene diradical thereto, as well as a stable N-oxide thereof.

Particular values are listed below for radicals, substituents and ranges for a compound of formula I as described above for illustration only and they do not exclude other defined values or other values within defined ranges for the radicals and substituents.

A particular value for Ar is phenyl which may be unsubstituted or may bear a chloro, methyl, methoxy, hydroxy or methylsulfinyl substituent. A particular value for Het is furyl, thienyl, 2-imidazolyl, 1,3,4-oxadiazol-2-yl, pyridyl or pyrimidinyl which ring may be unsubstituted or may bear a chloro, methyl, methoxy, hydroxy, methylsulfinyl, methoxycarbonyl or ethoxycarbonyl substituent. A particular value for aryl is phenyl. A particular value for heteroaryl is furyl, pyridyl or pyrimidinyl. A particular value for halo is chloro or bromo. A particular value for (1–3C)alkyl is methyl, ethyl, propyl or isopropyl; for (1–4C)alkyl is methyl, ethyl, propyl, isopropyl, butyl, isobutyl or t-butyl; for (1–5C)alkyl is methyl, ethyl, propyl, isopropyl, butyl, isobutyl, t-butyl, pentyl or isopentyl; for (1–6C)alkyl is methyl, ethyl, propyl, isopropyl, butyl, isobutyl, t-butyl, pentyl, isopentyl, hexyl or isohexyl; and for (1–8C)alkyl is methyl, ethyl, propyl, isopropyl, isopentyl, 1-ethylpropyl, hexyl, isohexyl, 1-propylbutyl, or octyl. A particular value for (3–6C)cycloalkyl is cyclopropyl, cyclopentyl or cyclohexyl; for (3–7C)cycloalkyl is cyclopropyl, cyclopentyl, cyclohexyl or cycloheptyl; and for (3–8C)cycloalkyl is cyclopropyl, cyclopentyl, cyclohexyl, cycloheptyl or cyclooctyl. A particular value for (3–6C)alkenyl is allyl, 2-butenyl or 3-methyl-2-butenyl. A particular value for (1–4C)alkanoyl is formyl, acetyl, propionyl, butyryl or isobutyryl; and for (1–5C)alkanoyl is formyl, acetyl, propionyl, butyryl, isobutyryl, valeryl, isovaleryl or pivaloyl.

A more particular value for Ar is phenyl which may be unsubstituted or may bear a methoxy, hydroxy or methylsulfinyl substituent. A more particular value for Het is pyridyl or pyrimidinyl which ring may be unsubstituted or may bear a methoxy, hydroxy or methylsulfinyl substituent. A more particular value for heteroaryl is pyridyl. A more particular value for halo is chloro. A more particular value for (1–3C)alkyl is methyl; for (1–4C)alkyl is methyl or ethyl; for (1–5C)alkyl is methyl, ethyl, propyl or isopropyl; for (1–6C)alkyl is methyl, ethyl, propyl, isopropyl, butyl, isobutyl or t-butyl; and for (1–8C)alkyl is methyl, ethyl, propyl, isopropyl, 1-ethylpropyl or 1-propylbutyl. A more particular value for (3–6C)cycloalkyl is cyclopropyl or cyclopentyl; for (3–7C)cycloalkyl is cyclopropyl or cyclopentyl; and for (3–8C)cycloalkyl is cyclopropyl, cyclopentyl, cyclohexyl or cycloheptyl. A more particular value for (3–6C)alkenyl is allyl. A more particular value for (1–4C)alkanoyl is formyl or acetyl; and for (1–5C)alkanoyl is formyl, acetyl, propionyl, butyryl or isobutyryl.

A particular value for $Q^1$ is 4-hydroxy-4-phenylpiperidino, 4-acetamido-4-phenylpiperidino, 4-(benzylsulfinyl)-4-methoxypiperidino, 4-(2-methylsulfinylphenyl)piperidino, or 4-(2-oxoperhydropyrimidin-1-yl)piperidino; $Q^2$ is methyl, ethyl or propyl; for $Q^3$ is hydrogen; for $Q^4$ is 3,4-dichlorophenyl or 3,4-methylenedioxyphenyl; and for $Q^5$ is phenyl, benzyl, 2-methoxyphenyl, 3,5-bis(trifluoro-methyl)benzyl, 2-isopropoxybenzyl and 3,5-bis(trifluoromethyl)phenyl.

A particular group of compounds of formula I are compounds wherein $Q^1$ is a radical selected from the group of radicals of formulae Ia, Ib, Ic, Ie, If, Ig, Ih, Ij, Ik and Im, A particular group of compounds of formula I are compounds wherein $Q^1$ is selected from radicals of formulae Ie, If, Ig, Ih, Ij Ik and Im.

A particular group of compounds of formula I are compounds of formula VIII wherein, $Q^1$ is 4-hydroxy-4-phenylpiperidino, 4-acetamido-4-phenylpiperidino, 4-(benzylsulfinyl)-4-methoxypiperidino, or 4-(2-oxoperhydropyrimidin-1-yl)piperidino; $Q^2$ is (1–3C)alkyl; and $Q^5$ is phenyl, benzyl, 2-methoxyphenyl, 2-methoxybenzyl, 3,5-bis(trifluoromethyl)phenyl, 3,5-bis (trifluoromethyl)benzyl, 3,5-dimethylphenyl, 3,5-dimethylbenzyl, 3,5-dichlorophenyl, 3,5-dichlorobenzyl, 3,5-dimethoxyphenyl, or 3,5-dimethoxybenzyl.

A particular group of compounds of formula I are compounds wherein $Q^5$ is formyl, 4-imidazolidinyl, 3-pyrrolidinyl (wherein the nitrogen may optionally be substituted by a substituent selected from (1–3C)alkyl, acyl, and benzyloxycarbonylaminoacetyl), (3–6C)cycloalkyl, trifluoromethyl, 4-piperidino (wherein the nitrogen may optionally be substituted by a substituent selected from (1–3C)alkyl, and acyl), aryl, heteroaryl pyrid-1-ylmethyl, fluorenyl, β-styryl, a radical of formula XII–XXII or xanthenyl; or $Q^5$ is (1–6C)alkyl which may be substituted by one substituent selected from aryl, heteroaryl, (aryl)oxy, (heteroaryl)oxy, benzyloxy, (3–6C)cycloalkyl, adamantyl, norbornanyl, β-styryl, cyano, trifluoromethyl, oxo, hydroxy, (1–4C)alkoxy, $—NR^a R^b$, $—NC(=O)NR^c R^d$, $—NC(=O)OR^e$, $—C(=O)OR^f$, $—S(O)R^g$, $—S(O)_2 R^h$, $=NR^i$, $SR^j$, and the radicals of formulae XII–XXII.

A more particular group of compounds of formula I are compounds of formula VIII wherein, $Q^1$ is 4-hydroxy-4-phenylpiperidino; $Q^2$ is (1–3C)alkyl; and $Q^5$ is phenyl, benzyl, 2-methoxyphenyl, 3,5-bis(trifluoromethyl)benzyl, 2-isopropoxybenzyl or 3,5-bis(trifluoromethyl)phenyl.

Another more particular group of compounds of formula I are compounds of formula VIII wherein, $Q^1$ is 4-hydroxy-4-phenylpiperidino; $Q^2$ is methyl; and $Q^5$ is phenyl, benzyl, 2-methoxyphenyl, 2-methoxybenzyl, 3,5-bis (trifluoromethyl)phenyl, 3,5-bis(trifluoromethyl)benzyl, 3,5-dimethylphenyl, 3,5-dimethylbenzyl, 3,5-dichlorophenyl, 3,5-dichlorobenzyl, 3,5-dimethoxyphenyl, or 3,5-dimethoxybenzyl.

Pharmaceutically acceptable salts of a compound of formula I include those made with a strong inorganic or organic acid which affords a physiologically acceptable anion, such as, for example, hydrochloric, sulfuric, phosphoric, methanesulfonic, or para-toluenesulfonic acid.

A compound of formula I may be made by processes which include processes known in the chemical art for the production of structurally analogous heterocyclic compounds. Such processes and intermediates for the manufacture of a compound of formula I as defined above are provided as further features of the invention and are illustrated by the following procedures in which the meanings of generic radicals are as defined above unless otherwise indicated:

(a) acylation of an amine of formula IV with an acid chloride of formula V wherein X is chloro. The acylation may conveniently be carried out in an inert solvent such as for example dimethylformamide, dichloromethane, chloroform, tetrahrdrofuran, toluene or diethyl ether, at a temperature in the range of –50° to 100° C., preferably in the range of –20° to 50° C.; and may conveniently be carried out in the presence of a suitable base. Suitable conditions for the acylation of an amine of formula IV are described in Example 1.

(b) acylation of an amine of formula IV with an acid of formula V wherein X is OH. The reaction may be carried out in the presence of a suitable coupling reagent, such as for example 1,1'carbonyldiimidazole, in an inert solvent, such as for example tetrahydrofuran, toluene or diethyl ether, at a temperature in the range of –50° to 100° C., preferably in the range of 0° to 50° C. Suitable conditions for the acylation of an amine of formula IV are described in Example 2.

(c) for a compound of formula I wherein $Q^2$ is (1–3C) alkyl, alkylating a corresponding compound of formula I wherein $Q^2$ is hydrogen with a compound of formula $Q^2 Y$ wherein Y is a suitable leaving group such for example chloro, bromo or methanesulfonyl. The alkylation may conveniently be carried out in an inert solvent such as for example dichloromethane, chloroform, tetrahrdrofuran, toluene or diethyl ether, at a temperature in the range of –50° to 100° C., preferably in the range of –20° to 50° C., and may conveniently be carried out in the presence of a suitable base. Suitable conditions for the alkylation of a compound of formula I are described in Example 3.

(d) For an N-oxide of a piperidino nitrogen in $Q^1$ indicated by Δ in formulae Ia–Im (or of either basic piperazinyl nitrogen of $Q^1$ when $Z^a$ is nitrogen); oxidizing the piperidino nitrogen of a corresponding compound of formula I using a conventional procedure, such as, for example, using hydrogen peroxide in methanol, peracetic acid, 3-chloroperoxybenzoic acid in an inert solvent (such as dichloromethane) or dioxirane in acetone.

(e) For a quaternary ammonium salt of the piperidino nitrogen in $Q^1$ indicated by Δ in formulae Ia–Im (or either basic piperazinyl nitrogen of $Q^1$ when $Z^a$ is nitrogen), alkylating the piperidino nitrogen in a corresponding compound of formula I with an alkylating agent of formula $R^1 Y$ wherein Y is a leaving group.

(f) For a compound of formula I which bears a sulfinyl group, oxidizing the sulfur of a corresponding compound of formula I which bears a sulfide group using a conventional method.

(g) For a compound of formula I which bears a sulfonyl group, oxidizing a sulfide or sulfinyl group of a corresponding compound of formula I using a conventional method.

(h) For a compound of formula I which bears an aromatic hydroxy group, cleaving the ether of a corresponding compound of formula I which bears an aromatic alkoxy group using a conventional method.

It may be desired to optionally use a protecting group during all or portions of the above described processes; the protecting group then may be removed when the final compound is to be formed.

Whereafter, for any of the above procedures, when a pharmaceutically acceptable salt of a compound of formula I is required, it may be obtained by reacting the compound of formula I with an acid affording a physiologically acceptable counterion or by any other conventional procedure.

It will also be appreciated that certain of the various optional substituents in the compounds of the invention may be introduced by standard aromatic substitution reactions or generated by conventional functional group modifications either prior to or immediately following the processes above, and as such are included in the process aspect of the invention. The reagents and reaction conditions for such procedures are well known in the chemical art.

If not commercially available, the necessary starting materials for the above procedures may be made by procedures which are selected from standard techniques of organic chemistry, techniques which are analogous to the synthesis of known, structurally similar compounds and techniques which are analogous to the above described procedures or the procedures described in the Examples. The starting materials and the procedures for their preparation are additional aspects of the invention.

A convenient intermediate for the preparation of a compound of formula I is an amine of formula IV, which can be prepared as shown in Scheme I, from a piperidine of formula $Q^1$—H, wherein $Q^1$ is selected from formulae Ia–Im. Coupling of an aldehyde of formula VI with trimethylsilylcyanide and a piperidine of formula $Q^1$—H in the presence of catalytic zinc iodide gives a nitrile of formula VII. Reduction of the nitrile yields an amine of formula IV, wherein $Q^2$ is hydrogen.

Piperidines of formula $Q^1$—H can be pepared from readily available starting materials using known synthetic methods. For example, the preparation of piperidines of formula $Q^1$—H is disclosed in European Patent Application, Publication Number (EPA) 428434, EPA 474561, EPA 512901, EPA 512902, EPA 515240 and EPA 559538, as well as in WO 94/10146. As will be clear to one skilled in the art, a variety of sequences are available for preparation of the starting materials, and the sequences leading to the starting materials and products of the invention may be altered if appropriate considerations regarding the synthetic methods and radicals present are followed.

The utility of a compound of the invention or a pharmaceutically acceptable salt thereof (hereinafter, collectively referred to as a "Compound") may be demonstrated by standard tests and clinical studies, including those disclosed in the EPA publications noted above, and those described below.

SP Receptor Binding Assay (Test A)

The ability of a Compound of the invention to antagonize the binding of SP at the NK1 receptor may be demonstrated using an assay using the human NK1 receptor expressed in Mouse Erythroleukemia (MEL) cells. The human NK1 receptor was isolated and characterized as described in: B. Hopkins, et al. "Isolation and characterization of the human lung NK1 receptor cDNA" *Biochem. Biophys. Res. Comm.*, 1991, 180, 1110–1117; and the NK1 receptor was expressed in Mouse Erythroleukemia (MEL) cells using a proceedure similar to that described in Test B below.

In general, the Compounds of the invention which were tested demonstrated statistically significant binding activity in Test A with a $K_i$ of 1 μM or much less typically being measured.

Neurokinin A (NKA) Receptor Binding Assay (Test B)

The ability of a Compound of the invention to antagonize the binding of NKA at the NK2 receptor may be demonstrated using an assay using the human NK2 receptor expressed in Mouse Erythroleukemia (MEL) cells, as described in: Aharony, D., et al. "Isolation and Pharmacological Characterization of a Hampster Neurokinin A Receptor cDNA" *Molecular Pharmacology*, 1994, 45, 9–19. In an initial use of this assay, the $IC_{50}$ measured for the standard compound L-659,877 was found to be 30 nM versus $^3$H-NKA binding to MELM.

The selectivity of a Compound for binding at the NK1 and the NK2 receptors may be shown by determining its binding at other receptors using standard assays, for example, one using a tritiated derivative of NKB in a tissue preparation selective for NK3 receptors. In general, the Compounds of the invention which were tested demonstrated statistically significant binding activity in Test B with a $K_i$ of 10 μM or less typically being measured.

Rabbit Pulmonary Artery: NK1 in vitro functional assay (Test C)

The ability of a Compound of the invention to antagonize the action of the agonist, Ac-[Arg$^6$, Sar$^9$, Met(O$_2$)$^{11}$]SP (6–11) (designated ASMSP) in a pulmonary tissue may be demonstrated using a functional assay which is carried out under conditions similar to those described in: Emonds-Alt, X., et al. "In vitro and in vivo biological activities of Sr 140333, a novel potent non-peptide tachykinin NK$_1$ receptor antagonist" *Eur. J. Pharmacol.*, 1993, 250, 403–413; and which is carried out as follows.

Male New Zealand white rabbits are killed by lethal injection (Nembutal, 60 mg/kg into a cannulated ear vein). Heparin, 0.0025 ml/kg of a 1000 U/ml solution, is injected into the ear vein prior to nembutal in order to decrease blood coagulation. The left and right branches of the pulmonary artery are isolated from the rest of the lung tissue and cut in half to provide four ring segments from each animal. The segments, with intact endothelium, are suspended between stainless steel stirrups and placed in water-jacketed (37.0° C.) tissue baths containing physiological salt solution of the following composition (mM): NaCl, 119.0; KCl 14.6; CaCl$_2$, 1.8; MgCl$_2$, 0.5; NaH$_2$PO$_4$, 1.0; NaHCO$_3$, 25.0; glucose 11.0; indomethacin 0.005 (to inhibit cyclooxygenase); and dl-propranolol, 0.001 (to inhibit β-adrenergic receptors); gassed continuously with 95% O$_2$–5% CO$_2$. Initial tension placed on each tissue is 2 grams, which is maintained throughout a 0.5 hour equilibration period. Changes in tension are measured on a Grass polygraph via Grass FT-03 force transducers.

Thiorphan, $1\times10^{-6}$M (to inhibit E.C.3.4.24.11), and a selective NK2 antagonist (to inhibit NK$_2$ receptors) such as for example, an antagonist described in WO 94/148,184, EPA 0625509, EPA 0630887, or the antagonist SR48968 ($3\times10^{-8}$M), are added to the tissue baths along with the test compound or its vehicle 90 minutes before the NK$_1$ receptor agonist, Ac-[Arg$^6$, Sar$^9$, Met(O$_2$)$^{11}$]SP(6–11) (designated ASMSP). Phenylephrine, $3\times10^{-6}$M, is added in order to induce tone in the tissue. One hour after introducing phenylephrine, cumulative concentration response effects of ASMSP are obtained and papaverine, $1\times10^{-3}$M, is added at the end of each experiment to determine the maximum magnitude of relaxation (defined as 100%).

Potencies of the compounds are determined by calculating the apparent dissociation constants ($K_B$) for each concentration tested using the standard equation:

$$K_B = [\text{antagonist}]/(\text{dose ratio}-1)$$

where dose ratio=antilog[(agonist–log molar $EC_{50}$ without compound)–(agonist–log molar $EC_{50}$ with compound)]. The $K_B$ values are converted to the negative logarithms and expressed as –log molar $K_B$ (i.e. p$K_B$). The potency of the agonist is determined at 50% of its own maximum relaxation in each curve. The $EC_{50}$ values are converted to negative logarithms and expressed as –log molar $EC_{50}$. Maximum relaxation responses to ASMSP are determined by expressing the maximum response to the agonist as a percentage of the relaxation caused by papaverine.

Guinea Pig Trachea Assay: NK2 in vitro functional assay (Test D)

The ability of a Compound of the invention to antagonize the action of the agonist, [β-Ala8]-Neurokinin A(4–10) (designated BANK), in a pulmonary tissue may be demonstrated using a functional assay in guinea pig trachea which is carried out under conditions similar to those described in: Ellis, J. L., et al., "Pharmacological examination of receptors mediating contractile responses to tachykinins in airways isolated from human, guinea pig and hamster" *J. Pharmacol. Exp. Ther.*, 1993, 267, 95–101; and which is carried out as follows.

Male guinea pigs are killed by a sharp blow to the back of the head followed by exsanguination. The trachea are removed, trimmed of excess tissue (including removal of epithelium) and cut in spiral fashion. Each longitudinally cut tracheal segment is suspended as a strip in a water-jacketed (37.5° C.) tissue bath containing a physiological salt solution of the following composition (mM): NaCl, 119; KCl 4.6; $CaCl_2$, 1.8; $MgCl_2$, 0.5; $NaH_2PO_4$, 1; $NaHCO3$, 25; glucose, 11; and indomethacin, 0.005 (to inhibit cyclooxygenase); gassed continuously with 95% $O_2$–%5 $CO_2$. Initial tension placed on each tissue is 5 g, which is maintained throughout a 0.5 hour equilibration period before addition of other drugs. Contractile responses are measured on a Grass polygraph via Grass FT-03 force transducers.

Tissues are challenged once with a single concentration of capsaicin ($1\times10^{-6}$M) and washed extensively before addition of a selective NK1 antagonist, such as for example ($\pm$)-CP96345 ($3\times10^{-7}$M) (to block NK1 receptors) and thiorphan, $1\times10^{-6}$M (to block E.C.3.4.24.11). Cumulative addition of the $NK_2$ agonist [β-Ala8]-Neurokinin A(4–10) (designated BANK) is begun 35 minutes after addition of thiorphan. Test compound is added 120 min before BANK.

Potencies of the compounds are evaluated by calculating apparent dissociation constants ($K_B$) for each concentration tested using the standard equation:

$$K_B=[\text{antagonist}]/(\text{dose ratio}-1)$$

where dose ratio=antilog[(agonist –log molar $EC_{50}$ without compound)–(agonist –log molar $EC_{50}$ with compound)]. The $K_B$ values are converted to the negative logarithms and expressed as –log molar $K_B$(i.e. $pK_B$). The potency of BANK is determined at 50% of its own maximum response level in each curve. The $EC_{50}$ values are converted to the negative logarithms and expressed as –log molar $EC_{50}$. Maximum contractile responses to BANK are determined by expressing the maximum response to BANK as a percentage of the initial contraction caused by capasacin.

In general, the Compounds of the invention which were tested demonstrated functional activity in Tests C and D, with a pKB of 5 or greater typically being measured in each test. For Example, the compound of Example 2 demonstrated a pKB of 6.2 in Test C.

Guinea Pig Labored Abdominal Breathing (Dyspnea) Assay: $NK_1$ and $NK_2$ in vivo functional assay (Test E)

The activity of a compound as an antagonist of $NK_1$ or $NK_2$ receptors also may be demonstrated in vivo in laboratory animals, for example by adapting a routine guinea pig aerosol test described for evaluation of leukotriene antagonists in: Snyder, et al. "Conscious guinea-pig aerosol model for evaluation of peptide leukotriene antagonists" *J. Pharmacol. Meth.*, 1988, 19, 219, which is carried out as follows.

Using the clear plastic chamber described previously by Snyder et al. to secure guinea pigs for a head-only aerosol exposure to bronchoconstrictor agonists, agonist is administered by aerosol to six conscious guinea pigs simultaneously during each maneuver. The tachykinin $NK_1$-selective agonist ASMSP or the tachykinin $NK_2$-selective agonist, BANK, $3\times10^{-5}$M of either, is aerosolized from a Devilbiss Model 25 ultrasonic nebulizer into an air stream entering the chamber at a rate of 2 L/minute.

Guinea pigs (275–400 g) are fasted for approximately 16 hours prior to experimentation. Compounds to be evaluated for blockade of effects of ASMSP or BANK or their vehicle (10% PEG400 in saline) are given by p.o., i.v. or aerosol routes of administration at various times before aerosol agonist challenge. All animals are pretreated with atropine (10 mg/kg, i.p., 45 minutes pretreatment) indomethacin (10 mg/kg, i.p. 30 minutes pretreatment), propranolol (5 mg/kg, i.p., 30 minutes pretreatment), and thiorphan (1 mg/ml aerosol for 5 minutes, 15 minutes pretreatment).

Aerosol challenge with the agonist produces an initial increase in respiratory rate followed by a decrease with early signs of minor involvement of the abdominal muscles. The respiratory rate decreases further and the breathing becomes more labored with greater involvement of the abdominal muscles as exposure continues. The distinctly recognizable end point is the point where the breathing pattern of the guinea pig is consistently slow, deep, and deliberate, showing marked involvement of the abdominal muscles. Time, in seconds, from the onset of aerosol challenge to this end point is determined for each animal by using a stopwatch. The animals generally collapsed after reaching the end point and did not recover from the agonist-induced respiratory distress. Antagonists result in an increase in the time to reach the end point. Animals receive the aerosol administration of agonist for a maximum time of 780 seconds.

Differences between drug-treated groups and corresponding vehicle-treated control groups are compared using Student's t-test for unpaired observations. Results are reported as % protection values, where % protection=

$$[(\text{drug time} - \text{mean control time})/(\text{maximal aerosol time} - \text{mean control time})]\times 100$$

Clinical Studies

Clinical studies to demonstrate the efficacy of a Compound of the invention may be carried out using standard methods. For example, the ability of a Compound to prevent or treat the symptoms of asthma or asthma-like conditions may be demonstrated using a challenge of inhaled cold air or allergen and evaluation by standard pulmonary measurements such as, for example, $FEV_1$ (forced expiratory volume in one second) and FVC (forced vital capacity), analyzed by standard methods of statistical analysis.

It will be appreciated that the implications of a Compound's activity in the above desribed Tests is not limited to asthma, but rather, that the Tests provide evidence of general antagonism of both SP and NKA SP and NKA have been implicated in the pathology of numerous diseases including: rheumatoid arthritis, Alzheimer's disease, cedema, allergic rhinitis, inflamation pain, gastrointestinal-hypermotility, irritable bowel syndrome, anxiety, emesis, Huntington's Disease, Psycoses, hypertension, migraine, urinary incontinence, bladder hypermotility, and uticaria. Accordingly, one feature of the invention is the use of a compound of formula I or a pharmaceutically acceptable salt thereof in the treatment of a disease in a human or other mammal in need thereof in which SP or NKA is implicated and antagonism of its action is desired.

Asthma is characterized symptomatically by both chronic inflammation and hyperresponsiveness of the airways. The NK1 receptor is known to mediate inflammation and mucus hypersecretion in airways; and the NK2 receptor is involved in the control of the tone of bronchial smooth muscle. Thus, agents capable of antagonizing the actions of SP and NKA, at the NK1 and NK2 receptors, respectively, are capable of reducing both the chronic inflammation and the airway hyperresponsiveness which are symptomatic of asthma. Additionally, a synergistic effect against bronchoconstriction may result from the simultaneous application of an NK1 antagonist and an NK2 antagonist. D. M. Foulon, et al. "NK1 and NK2 Receptors Mediated Tachykinin and Resiniferatoxin-induced Bronchospasm in Guinea Pigs" *American Review of Respiratory Disease*, 1993, 148, 915–921. Accordingly, another feature of the invention is the use of a compound of formula I or a pharmaceutically acceptable salt thereof in the treatment of asthma in a human or other mammal in need thereof.

Because of the range of effects attributable to the actions of SP and NKA, compounds which are capable of blocking their actions may also be useful as tools for further evaluating the biological actions of other neurotransmitters in the Tachykinin family. As a result, another feature of the invention is provided by the use of a compound of formula I or a salt thereof as a pharmacological standard for the development and standardization of new disease models or assays for use in developing new therapeutic agents for treating diseases in which SP or NKA are implicated or for assays for their diagnosis.

When used in the treatment of a disease, a compound of the invention is generally administered as an appropriate pharmaceutical composition which comprises a compound of formula I or a pharmaceutically acceptable salt thereof as defined hereinbefore and a pharmaceutically acceptable diluent or carrier, the composition being adapted for the particular route of administration chosen. Such a composition is provided as a further feature of the invention. It may be obtained employing conventional procedures and excipients and binders, and it may be one of a variety of dosage forms. Such forms include, for example, tablets, capsules, solutions or suspensions for oral administration; suppositories for rectal administration; sterile solutions or suspensions for administration by intravenous or intramuscular infusion or injection; aerosols or nebulizer solutions or suspensions for administration by inhalation; or powders together with pharmaceutically acceptable solid diluents such as lactose for administration by insufflation.

For oral administration a tablet or capsule containing up to 250 mg (and typically 5 to 100 mg) of a compound of formula I may conveniently be used. For administration by inhalation, a compound of formula I will be administered to humans in a daily dose range of, for example, 5 to 100 mg, in a single dose or divided into two to four daily doses. Similarly, for intravenous or intramuscular injection or infusion a sterile solution or suspension containing up to 10% w/w (and typically 0.05 to 5% w/w) of a compound of formula I may conveniently be used.

The dose of a compound of formula I to be administered will necessarily be varied according to principles well known in the art taking account of the route of administration and the severity of the condition and the size and age of the patient under treatment. However, in general, the compound of formula I will be administered to a warm-blooded animal (such as man) so that a dose in the range of, for example, 0.01 to 25 mg/kg (and usually 0.1 to 5 mg/kg) is received. It will be understood that generally equivalent amounts of a pharmaceutically acceptable salt of a compound of formula I may be used.

The invention will now be illustrated by the following non-limiting examples in which, unless stated otherwise:

(i) temperatures are given in degrees Celsius (°C); operations were carried out at room or ambient temperature, that is, at a temperature in the range of 18°–25 ° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60 ° C.;

(iii) chromatography means chromatography on silica gel; thin layer chromatography (TLC) was carried out on silica gel plates;

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory proton nuclear magnetic resonance (NMR) spectra;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent; conventional abbreviations for signal shape are used; for AB spectra the directly observed shifts are reported; coupling constants (J) are given in Hz; Ar designates an aromatic proton when such an assignment is made;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms;

and (xii) mass spectra (MS) were run with an electron energy of 70 electron volts in the chemical ionization (CI) mode using a direct exposure probe; where indicated ionization was effected by electron impact (EI) or fast atom bombardment (FAB); values for m/z are given; generally, only ions which indicate the parent mass are reported.

EXAMPLE 1

N-[2-(3,4-Dichlorophenyl)-2-pyrrolidin-1-ylethyl] benzamide hydrochloride salt 2-(3,4-Dichlorophenyl)-2-(pyrrolidin-1-yl)ethylamine (2.46 g), benzoyl chloride (1.34 g) and triethylamine (1.92 g) were stirred in dichloromethane (25 mL) at 23° C., for 48 hours. The reaction was poured into water, and the seperated organic layer was dried, and evaporated to a brown oil (2.85 g). Chromatography, with chloroform (1200 mL) and then methanol:chloroform (5:95) as the eluent, gave an oil. Trituration of the oil with diethylether gave a white solid which was dissolved in dichloromethane and treated with hydrochloric acid (g)/diethylether. The solution was evaporated to give the title compound as a white glass (330 mg); mp 129° C. (after resolidifing); MS: m/z=636(M+11); NMR: 1.78 (m, 4), 2.54 (m,4), 3.5 (m,2), 4 (m,1), 6.16 (broad s,1), 7.21 (m,1), 7.42 (m,5), 7.62 (m,2): Analysis Calculated: C, 55.22; H, 5.49; N, 6.78; Found: C, 55.21; H, 5.24; N, 6.59.

The intermediate 2-(3,4-dichlorophenyl)-2-(pyrrolidin-1-yl)ethylamine was prepared as follows.

a) α-Pyrrolidin-1-yl-3,4-dichlorobenzyl cyanide hydrochloride salt. Trimethylsilylcyanide (2.02 g) and catalytic zinc iodide were added to a solution of 3,4- dichlorobenzaldehyde (2.86 g) in dichloromethane (40 mL) at 23° C. The reaction was stirred at 23° C. for 20 minutes and treated with a solution of pyrrolidine (1.16 g) in methanol (20 mL). The reaction was refluxed for 2 hours and stirred 18 hours at 23° C. The reaction was cooled in an ice bath and treated with hydrochloric acid (g)/methanol (pH=1 to 2). The reaction was stirred at 23° C. for 1 hour and evaporated to a gold oil which was used directly in the next reaction.

b) 2-(Pyrrolidin-1-yl)-2-(3,4-dichlorophenyl)ethylamine. A slurry of α-Pyrrolidin-1-yl-3,4-dichlorobenzyl cyanide hydrochloride salt (4.73 g) in tetrahydrofuran (100 mL) was added to a slurry of lithium aluminum hydride (3.23 g) in tetrahydrofuran (35 mL) while maintaining a reflux. The reaction was allowed to reflux 18 hours. The reaction was cooled in an ice bath and treated with aqueous sodium sulfate. The reaction was filtered and evaporated to give a reddish-brown oil. The oil was dissolved in diethylether, treated with hydrochloric acid (g)/diethylether, and evaporated to a red oil which was used directly in subsequent reactions.

EXAMPLE 2

N-[2-(3,4-Dichlorophenyl)-2-(4-hydroxy-4-phenylpiperidino)ethyl]-N-methyl-2-methoxyphenylacetamide hydrochloride salt A solution of 2-methoxyphenyl acetic acid (570 mg) and 1,1'carbonyldiimidazole (610 mg) in tetrahydrofuran (10 mL) was stirred at reflux for 0.5 hours. The reaction was cooled to 23° C. and treated with a solution of N-[2-(3,4-dichlorophenyl)-2-(4-hydroxy-4-phenylpiperdino)ethyl]methylamine (940 mg) in tetrahydrofuran (50 mL). The reaction was stirred at 23° C. for 18 hours. The reaction was evaporated to a gold oil. The oil was dissolved in dichloromethane (30 mL), treated with hydrochloric acid (g)/ether, and evaporated to a yellow oil, which was dissolved in dichloromethane (10 mL) and added dropwise to diethylether (500 mL). The title compound precipitated as a white solid; mp 205°–208° C.; MS: m/z=527 (M+1); NMR: 1.75 (m,2), 2.43 (m, 1), 2.6 (m, 1), 2.81 (s,3), 3.12 (m,3), 3.48 (m,4), 3.69 (s,3), 3.76 (m,4), 4.17 (m, 1), 4.35 (m, 1), 4.79 (m, 1), 6.67 (d,1), 6.77 (d,1,), 7.31 (m,6), 7.76 (m,2), 8.05 (s,1), 11.66 (s,1,) 11.73 (s,1). Analysis Calculated: C, 61.76; H, 5.9; N, 4.97; Found: C, 61.68; H, 5.96; N, 4.91.

The intermediate N-[2-(3,4-dichlorophenyl)-2-(4-hydroxy-4-phenylpiperdino)ethyl]methylamine was prepared as follows.

a) α-(4-Hydroxy-4-phenylpiperidino)-3,4-dichlorobenzyl cyanide hydrochloride salt. Trimethylsilylcyanide (2.02 g) and catalytic zinc iodide were added to a solution of 3,4-dichlorobenzaldehyde (2.86 g) in dichloromethane (45 mL) at 23° C. The reaction was stirred at 23° C. for 20 minutes and treated with a solution of 4-hydroxy-4-phenylpiperdine (2.89 g) in methanol (20 mL). The reaction was refluxed for 2.5 hours and stirred 18 hours at 23° C. The reaction was cooled in an ice bath and treated with hydrochloric acid (g)/ether (pH=1 to 2). The reaction was stirred at 23° C. for 1 hour and evaporated give to a tan oil. Trituration of the oil with ether:hexane:ethanol (1:1:1) gave the title compound as a pale yellow solid (5.09 g) which was used directly in subsequent reactions; MS: m/z=361(M+1).

b) 2-(3,4-Dichlorophenyl)-2-(4-hydroxy-4-phenylpiperdino)-ethylamine. A slurry of α-(4-hydroxy-4-phenylppiperidino)-3,4-dichlorobenzyl cyanide hydrochloride salt (5.09 g) in tetrahydrofuran (50 mL) was added to a slurry of lithium aluminum hydride (2.43 g) in tetrahydrofuran (40 mL) at reflux. After 18 hours, the reaction was cooled in an ice bath, treated with aqueous sodium sulfate, filtered, and dried (NaSO4), to give material which was used directly in subsequent reactions.

c) N-Acetyl-2-(3,4-dichlorophenyl)-2-(4-hydroxy-4-phenylpiperdino)ethylamine. A mixture of 2-(3,4-dichlorophenyl)-2-(4-hydroxy-4-phenylpiperdino) ethylamine (4.68 g) in tetrahydrofuran (200 mL), sodium carbonate (1.36 g) and methylchloroformate (1.21 g) was stirred at 23° C. for 48 hours. The reaction was evaporated, partitioned between dichloromethane (300 mL) and water (200 mL), and the seperated organic layer was dried and evaporated to give a gold oil, which was used directly in subsequent reactions.

d) N-[2-(3,4-Dichlorophenyl)-2-(4-hydroxy-4-phenylpiperdino)ethyl]methylamine. N-Acetyl-2-(3,4-dichlorophenyl)-2-(4-hydroxy-4-phenylpiperdino) ethylamine (5.40 g) in tetrahydrofuran (50 mL) was added to a slurry of lithium aluminum hydride (1.40 gm, 95%) in tetrahydrofuran while stirring at reflux. The reaction was allowed to reflux 18 hours, was cooled in an ice bath, treated with an aqueous solution of sodium sulfate, filtered, and dried (Na2SO4), to give material which was used directly in subsequent reactions.

EXAMPLE 3

N-[2-(3,4-Dichlorophenyl)-2-pyrrolidin-1-ylethyl]-N-methylbenzamide hydrochloride salt A solution of N-[2-(3,4-dichlorophenyl)-2-pyrrolidin-1-yl-ethyl]benzamide (260 mg) in dimethylsulfoxide (1.5 mL) and methyl iodide (230 mg) were added to a solution of KOH (190 mg) in dimethylsulfoxide (0.7 mL). The reaction was stirred at 23° C. for ¾ hour, was poured into water (10 mL), and extracted with dichloromethane (20 mL). The organic layer was washed (brine), dried and evaporated to a gold oil. Chromatography, with ethyl acetate:hexane (50:50 then 75:25) as the eluent, gave an oil, which was dissolved in diethylether and treated with hydrochloric acid (g)/diethylether to provide the title compound as a white solid (60 mg); mp 199°–202° C.; MS: m/z=377(M+1); NMR: 1.98 (m, 1), 2.12 (m,2), 2.35 (m, 1), 2.54 (s,3,), 2.61 (m, 1), 3.35 (m, 2), 3.88 (t,1), 4.13 (m, 1), 4.63 (m, 2), 7.2 (dd,1), 7.26 (s,1), 7.53 (d,1), 7.79 (broad s,1), 8.11 (broad s,1), 13.23 (broad s,1). Analysis Calculated: C, 57.43; H, 5.6; N, 6.7; Found: C, 57.59; H, 5.61; N, 6.35.

EXAMPLE 4

N-[2-(3,4-Dichlorophenyl)-2-(4-hydroxy-4-phenylpiperidino)ethyl]benzamide hydrochloride salt Benzoyl chloride (290 mg) and triethylamine (420 mg) were added to a solution of 2-(3,4-Dichlorophenyl)-2-(4-hydroxy-4-phenylpiperdino)ethylamine (750 mg) in tetrahydrofuran (37.5 mL). The reaction was stirred at 23° C. for 18 hours, and was evaporated to an oil-solid mixture. The mixture was partitioned between water (100 mL) and dichloromethane (100 mL), and the seperated organic layer was dried and evaporated to an off-white solid (1.01 gm). Treatment of a solution of this solid in diethylether with hydrochloric acid (g)/diethylether followed by recrystalization of the hydrochloride salt from ethylacetate (hot,minimum volume) provided the title compound as a white solid (450 mg); mp 232°–235° C.; MS: m/z=469(M+1); NMR: 1.8 (m, 2), 2.44 (m, 1), 2.63 (m, 1), 3.17 (m,3), 3.99 (m,2), 4.27 (m,1), 4.76 (m, 1), 5.4 (broad s,1), 7.26 (m,1), 7.46 (m,7), 7.8 (m, 5), 11.37 (broad s,1). Analysis Calculated: C, 61.73; H, 5.38; N, 5.54; Found: C, 61.8; H, 5.5; N, 5.52.

EXAMPLE 5

N-[2-(3,4-Dichlorophenyl)-2-(4-hydroxy-4-phenylpiperidino)ethyl]-N-methylbenzamide N-[2-(3,4-Dichlorophenyl)-2-(4-hydroxy-4-phenylpiperdino)ethyl]methylamine (450 mg), benzoyl chloride (168 mg), and triethylamine (120 mg) in tetrahydrofuran were stirred at 23° C. for 48 hours. The reaction was filtered concentrated to a gold oil. Chromatography, with chloroform and then methanol:chloroform (5:95) as the eluent, gave a gold oil. Trituration of the oil with diethylether/hexane provided a white solid; MS: m/z=483 (M+1); NMR: 1.77 (m,2), 2.4 (m, 1), 2.63 (m, 1), 2.72 (m,3), 3.2 (m#3), 3.83 (m,1), 4.36 (m,2), 4.93 (m, 1), 5.43 (broad s,1), 7.03 (m,2), 7.41 (m,7), 7.83 (m,2). Analysis Calculated: C, 60.28; H, 5.8; N, 5.21; Found: C, 60.25; H, 5.52; N, 5.14.

EXAMPLE 6

N-[2–3,4-Dichlorophenyl)-2-(4-hydroxy-4-phenylpiperidino)ethyl]phenylacetamide hydrochloride salt Phenyl acetylchloride (330 mg) and triethylamine (420 mg) were added to a solution of 2-(3,4-dichlorophenyl)-2-(4-hydroxy-4-phenylpiperdino)ethylamine (750 mg) in tetrahydrofuran (38 mL). The reaction was stirred at 23° C. for 18 hours, was evaporated to an oil-solid mixture, and was partitioned between water (100 mL) and dichloromethane (100 mL). The organic layer was dried and the filtrate evaporated to a gold oil. The oil was dissolved in diethylether and treated with hydrochloric acid (g)/diethylether. The ether layer was concentrated to a gold oil. The oil was partitioned between H2O (300 mL) and diethylether (300 mL). The aqueous layer was basified (ph=12) with sodium bicarbonate and extracted with diethylether (2×150 mL). This ether layer was treated with hydrochloric acid (g)/diethylether and concentrated to a gold oil. Trituration of the oil with diethylether provided the title compound as a tan glass (100 mg); mp 129°–133° C.: NMR: 1.77 (m, 2), 2.33 (m,2,), 3.13 (m, 4), 3.81 (m, 2), 4.04 (m, 1), 4.71 (m, 1), 5.39 (broad s,1), 7.02 (m,2), 7.33 (m,8), 7.61 (d,1), 7.75 (d,1), 8.1 (s,1), 8.5 (broad s,1), 10.94 (broad s,1). Analysis Calculated: C, 60.79; H, 5.76; N, 5.25; Found: C, 60.6; H, 5.47; N, 4.96.

EXAMPLE 7

N-[2-(3,4-Dichlorophenyl)-2-(4-hydroxy-4-phenylpiperidino)ethyl]-N-methylphenylacetamide hydrochloride salt N-[2-(3,4-Dichlorophenyl)-2-(4-hydroxy-4-phenylpiperdino)ethyl]methylamine (450 mg), phenylacetylchloride (190 mg) and triethylamine (120 mg) in tetrahydrofuran (25 mL) were stirred at 23° C. for 48 hours. The reaction was evaporated to a gold oil. Chromatography, with chloroform and then methanol:chloroform (5:95) as the eluent, provided a gold oil (420 mg). A solution of this oil in diethylether (15 mL) was treated with hydrochloric acid (g)/ether (4 mL) to give the title compound as a white solid (200 mg); mp 109 (some melt then resolidifies), 137°–139° C.; MS: m/z=497(M+1); NMR: 1.77 (m,2), 2.49 (m, 1), 2.65 (m,2), 2.81 (broad s,3), 3.05 (m,3), 3.56 (m,3), 4.17 (m,1), 4.32 (m,1), 4.74 (broad s,1), 6.96 (broad s,2), 7.33 (m,10), 7.67 (broad s,2), 8 (broad s,1), 11.64 (broad s,1). Analysis Calculated: C, 62.99; H, 5.66; N, 5.25; Found: C, 62.69; H, 5.9; N, 5.14.

EXAMPLE 8

N-[2-(3,4-Dichlorophenyl)-2-(4-hydroxy-4-phenylpiperidino)ethyl]-N-methyl-3,5-bis (trifluoromethyl)phenylacetamide hydrochloride salt A solution of 3,5-bis(trifluoromethyl)phenylacetic acid (1.61 g) and 1,1'-carbonyldiimidazole (1.01 g) in tetrahydrofuran (15 mL) was stirred at reflux for 0.5 hours. The reaction was cooled to 23° C. and treated with a solution of N-[2-(3,4-dichlorophenyl)-2-(4-hydroxy-4-phenylpiperdino)ethyl]methylamine (2.24 g) in tetrahydrofuran (70 mL). The reaction was stirred at 23° C. for 18 hours. The reaction was evaporated to an oil, and the oil was partitioned between diethylether and 1N hydrochloric acid (100 mL). The organic layer was treated with ethereal hydrochloric acid to produce the title compound as a white solid (950 mg); mp 230° C.; MS: m/z=633(M+1); NMR: 1.73 (m,2), 2.42 (m, 1), 2.75 (m, 1), 3.01 (s,4), 3.86 (m,4,), 4.43 (m, 1), 4.85 (m, 1), 5.34 (m, 1), 7.34 (m, 5), 7.73 (s 2), 7.87 (m,5), 8.06 (s,1), 11.36 (broad s,1). Analysis Calculated: C, 53.79; H, 4.36; N, 4.18; Found: C, 54.06; H, 4.48; N, 4.23.

EXAMPLE 9

N-[2-(3,4-Dichlorophenyl)-2-(4-hydroxy-4-phenylpiperidino)ethyl]-N-methyl-3-isopropoxyphenylacetamide hydrochloride salt A solution of 3-isopropoxyphenylacetic acid (670 mg) and 1,1'carbonyldiimidazole (590 mg) in tetrahydrofuran (15 mL) was stirred at reflux for 0.5 hours. The reaction was cooled to 23° C. and treated with a solution of N-[2-(3,4-dichlorophenyl)-2-(4-hydroxy-4-phenylpiperdino)ethyl] methylamine (940 mg) in tetrahydrofuran (40 mL). The reaction was stirred at 23° C. for 18 hours. The reaction was evaporated to a gold oil. The oil was partitioned between diethylether (100 mL) and 1N hydrochloric acid (150 mL). The organic layer was treated with hydrochloric acid (g)/ether and evaporated to give a yellow oil which was dissolved in dichloromethane (10 mL) and added dropwise to diethylether (500 mL). The title compound precipitated as a white solid (480 mg); mp 127°–132° C.; MS: m/z=555(M+ 1); NMR: 1.23 (d,3), 1.25 (d,3), 1.75 (m,2), 2.4 (m, 1), 2.7 (m,1), 2.83 (s,3), 3.13 (m,2), 3.43 (m,2), 3.54 (s,2), 3.73 (m, 1), 4.52 (m,1), 5.37 (m, 1), 6.38 (d,1), 6.66 (s,1,), 6.73 (d,1), 7.01 (m,3,), 7.22 (m, 2,), 7.46 (d,2), 7.7 (s,2,), 8.05 (s,1), 11.73 (s,1). Analysis Calculated: C, 61.95; H, 6.37; N, 4.66; Found: C, 61.94; H, 6.3; N, 4.56.

EXAMPLE 10

N-[2-(3,4-Dichlorophenyl)-2-(1,4-dioxa-8-azospiro (4.5)decan-8-yl)ethyl]-N-methyl-3-isopropoxyphenylacetamide A solution of 2-isopropoxyphenyl acetic acid (109 mg) and 1,1'carbonyldiimidazole (91 mg) in ethyl acetate (3 mL) was stirred once and reacted 1½ hours at 23° C. while under a blanket of nitrogen. The solution was treated with a solution of N-(methyl)-2-(3,4-dichlorophenyl)-2-(1,4-dioxa-8-azospiro(4.5)decan-8-yl)ethylamine (175 mg) in 2.5 mL of ethylacetate, stirred once and allowed to stand 24 hours under a blanket of nitrogen. Chromatography on a Varian Mega Bond Elute Si 1225-6034 column, 60 cc, 10 gm, MFG code 2217 with chloroform as the eluent gave the title compound; MS: m/z=521(M+1), HPLC purity 55%, rt=15.175. HPLC purity determined on a SPERISORB column (ODS 5u, purchased from Hewlet Packard, catalogue number 7992402-584) with a flow rate of 1.5 mL/minute, and an oven temp of 40° C., using UV detection (280nm). Two solvent systems were used to determine HPLC purity and they are designated Solvent A and Solvent B, herein. Solvent A is 1 mmol triethylamine in water, and Solvent B is 1 mmol triethylamine in acetonitrile. For the title compound, t=0–3 minutes, 95:5(A/B), t=17–20 minutes, 5:95(A/B), t=30 minutes 95:5(A/B).

a. α-(1,4-Dioxa-8-azospiro(4.5)decan-8-yl)-3,4-dichlorobenzyl cyanide. 3,4-Dichlorobenzaldehyde (2.59 g) in methanol (8 mL) was added to a solution of sodium bisulfite (1.54 g) in water (6 mL) at 23° C. under a nitrogen atmosphere. The mixture was cooled to 0–5° C., treated with 1,4-dioxa-8-azospiro(4.5)decane (2.12 g), followed by potassium cyanide (965 mg). The mixture was stirred in an ice-water bath and allowed to warm overnight to room temperature. The mixture was filtered and the resulting solid washed with methanol:water (1:1) to give the nitrile as a pale yellow solid, which was dried and used directly in subsequent reactions; MS: m/z=327(M+1); NMR: 1.75 (m, 4), 2.65 (t,4), 3.96 (s,4), 4.82 (s,1), 7.39 (d,1), 7.42 (d,1), 7.65 (s,1).

b. 2-(1,4-Dioxa-8-azospiro(4.5)decan-8-yl)-2-(3,4-dichlorophenyl)ethylamine A solution of (a) (11.00 g) in tetrahydrofuran (50 mL) was added to a slurry of lithium aluminum hydride (2.68 g, 95%) in tetrahydrofuran (100 mL) while maintaining a reflux while under a nitrogen atmosphere. The reaction was allowed to reflux for 18 hours. The solution was cooled in an ice bath and treated with aqueous sodium sulfate (saturated). The mixture was filtered, dried (NaSO$_4$), and the resulting material was used directly in subsequent reactions.

c. N-(Methoxycarbonyl)-2-(3,4-dichlorophenyl)-2-(1,4-dioxa-8-azospiro(4.5)decan-8-yl)ethylamine. A mixture of (b) (11.13 g) in tetrahydrofuran (300 mL), sodium carbonate (3.56 g) and methylchloroformate (3.18 g) was stirred at 23° C. for 18 hours while under a nitrogen atmosphere. The mixture was concentrated to an orange solid. The solid was partitioned between methylene chloride (200 mL) and water (200 mL). The organic layer was dried and concentrated under reduced pressure to a gold oil. The oil was used without further purification in subsequent reactions.

d. N-(Methyl)-2-(3,4-dichlorophenyl)-2-(1,4-dioxa-8-azospiro-(4.5)decan-8-yl)ethylamine. A solution of (c) (13.08 g) in tetrahydrofuran (50 mL) was added to a slurry of lithium aluminum hydride (2.61 g, 95%) in tetrahydrofuran (80 mL) while stirring at reflux under a nitrogen atmosphere. The solution was refluxed 18 hours, cooled in an ice bath and treated with an aqueous solution of sodium sulfate (saturated). The mixture was filtered, dried (Na$_2$SO$_4$), and used directly in subsequent reactions; MS: m/z=345(M+1).

EXAMPLES 11–23

Using a procedure similar to that described in Example 10 except replacing N-methyl-2-(3,4-dichlorophenyl)-2-(1,4-dioxa-8-azospiro(4.5)decan-8-yl)ethylamine with N-(methyl)-2-(3,4-dichlorophenyl)-2-(4-phenylpiperidino) ethylamine and replacing 2-isopropyloxyphenylacetic acid with the requisite carboxylic acid, the following compounds of formula I wherein $Q^1$ is 4-phenylpiperidino, $Q^2$ is methyl, $Q^3$ is hydrogen, $Q^4$ is dichlorophenyl, and $Q^5$ has the value defined were prepared.

EXAMPLE 11

$Q^5$=3,5-Bis(trifluoromethyl)benzyl; MS: m/z=617(M+1); HPLC: solvent method B, rt=15.946.

EXAMPLE 12

$Q^5$=3-Isopropoxybenzyl; MS: m/z=539(M+1); HPLC: Solvent B, rt=16.206.

EXAMPLE 13

$Q^5$=2,4-Diflurobenzyl; MS: m/z=517(M+1); HPLC: Solvent A, rt=18.504.

EXAMPLE 14

$Q^5$=2-Trifluoromethylbenzyl MS: m/z=549(M+1); HPLC: Solvent A, rt=19.009.

EXAMPLE 15

$Q^5$=3-Fluorobenzyl; MS m/z=499(M+1); HPLC: Solvent A, rt=18.464.

EXAMPLE 16

$Q^5$=2,5-Difluorobenzyl; MS: m/z=517(M+1); HPLC: Solvent A, rt=18.465.

EXAMPLE 17

$Q^5$=4-Trifluoromethylbenzyl; MS: m/z=549(M+1); HPLC: Solvent A, rt=15.591.

EXAMPLE 18

$Q^5$=3,5-Dichlorophenyl; MS: m/z=535,537,539(M+1); HPLC: Solvent A, rt=19.359.

EXAMPLE 19

$Q^5$=3,5-Dimethylphenyl; MS: m/z=495(M+1); HPLC: Solvent A, rt=19.245.

EXAMPLE 20

$Q^5$=Benzyl; MS: m/z=481(M+1); HPLC: Solvent B, rt=16.855.

EXAMPLE 21

$Q^5$=9-Xanthenyl; MS m/z=571(M+1); HPLC: Solvent B, rt=14.209.

EXAMPLE 22

$Q^5$=2-Methoxybenzyl; MS: m/z=511(M+1); Solvent A, rt=15.868.

EXAMPLE 23

$Q^5$=3,5-Dimethoxyphenyl; MS: m/z=527(M+1); Solvent A, rt=18.159.

EXAMPLES 24–36

Using a procedure similar to that described in EXAMPLE 10 except replacing N-methyl-2-(3,4-dichlorophenyl)-2-(1, 4-dioxa-8-azospiro(4.5)decan-8-yl)ethylamine with 2-(3,4- dichlorophenyl)-2-(4-hydroxy-4-phenylpiperidino)-N-(methyl)ethylamine and replacing 2-(isopropyloxy) phenylacetic acid with the requisite carboxylic acid, the following compounds of formula I wherein $Q^1$ is 4-hydroxy-4-phenyl-piperidino, $Q^2$ is methyl, $Q^3$ is hydrogen, $Q^4$ is dichlorophenyl, and $Q^5$ has the value defined were prepared.

EXAMPLE 24

$Q^5$=3,5-Bis(trifluoromethyl)benzyl; MS: m/z=633(M+1); HPLC: Solvent B, rt=14.059.

EXAMPLE 25

$Q^5$=3-Isopropoxybenzyl; MS: m/z=555(M+1); HPLC: Solvent B, rt=14.912.

EXAMPLE 26

$Q^5$=2,4-Diflurobenzyl; MS: m/z=533(M+1); HPLC: Solvent B, rt=14.181.

EXAMPLE 27

$Q^5$=2-Trifluoromethylbenzyl; MS: m/z=565(M+1); HPLC: Solvent B, rt=14.890.

EXAMPLE 28

$Q^5$=3-Fluorobenzyl; MS m/z=515(M+1); HPLC: Solvent B, rt=14.909.

EXAMPLE 29

$Q^5$=2,5-Difluorobenzyl; MS: m/z=533(M+1); HPLC: Solvent B, rt=14.311.

EXAMPLE 30

$Q^5$=4-Trifluoromethylbenzyl; MS: m/z=565(M+1); HPLC: Solvent B, rt=15.130.

EXAMPLE 31

$Q^5$=3,5-Dichlorophenyl; MS: m/z=551,553,555(M+1); HPLC: Solvent B, rt=15.282.

EXAMPLE 32

$Q^5$=3,5-Dimethylphenyl; MS: m/z=511(M+1); HPLC: Solvent B, rt=15.019.

EXAMPLE 33

$Q^5$=-Benzyl; MS: m/z=497(M+1); HPLC: Solvent B, rt=14.607.

EXAMPLE 34

$Q^5$=9-Xanthenyl; MS: m/z=587(M+1); HPLC: Solvent B, rt=15.182.

EXAMPLE 35

$Q^5$=2-Methoxybenzyl; MS: m/z=527(M+1); Solvent B, rt=14.378.

EXAMPLE 36

$Q^5$=3,5-Dimethoxyphenyl; MS: m/z=543 (M+1); Solvent B, rt=14.266.

EXAMPLES 37–49

Using a procedure similar to that described in EXAMPLE 10 except replacing N-methyl-2-(3,4-dichlorophenyl)-2-(1,4-dioxa-8-azospiro(4.5)decan-8-yl)ethylamine with 2-(3,4-dichlorophenyl)-2-(4-benzylpiperidino)-N-(methyl) ethylamine and replacing 2-(isopropyloxy)phenylacetic acid with the requisite carboxylic acid, the following compounds of formula I wherein $Q^1$ is 4-benzylpiperidino, $Q^2$ is methyl, $Q^3$ is hydrogen, $Q^4$ is dichlorophenyl, and $Q^5$ has the value defined were prepared.

EXAMPLE 37

$Q^5$=3,5-Bis(trifluoromethyl)benzyl; MS: m/z=631(M+1); HPLC: Solvent B, rt=18.7725.

EXAMPLE 38

$Q^5$=3-Isopropoxybenzyl; MS: m/z=553(M+1); HPLC: Solvent B, rt=18.945.

EXAMPLE 39

$Q^5$=2,4-Diflurobenzyl; MS: m/z=531(M+1); HPLC: Solvent A, rt=19.325.

EXAMPLE 40

$Q^5$=2-Trifluoromethylbenzyl; MS: m/z=563(M+1); HPLC: Solvent B, rt=19.195.

EXAMPLE 41

$Q^5$=3-Fluorobenzyl; MS: m/z=513(M+1); HPLC: Solvent B, rt=17.276.

EXAMPLE 42

$Q^5$=2,5-Difluorobenzyl; MS: m/z=531(M+1); HPLC: Solvent B, rt=18.663.

EXAMPLE 43

$Q^5$=4-Trifluoromethylbenzyl; MS: m/z=563(M+1); HPLC: Solvent B, rt=18.955.

EXAMPLE 44

$Q^5$=3,5-Dichlorophenyl; MS: m/z=549,551,553(M+1); HPLC: Solvent B, rt=19.570.

EXAMPLE 45

$Q^5$=3,5-Dimethylphenyl; MS: m/z=509(M+1); HPLC: Solvent B, rt=19.092.

EXAMPLE 46

$Q^5$=Benzyl; MS: m/z=495(M+1); HPLC: Solvent B, rt=18.592.

EXAMPLE 47

$Q^5$=9-Xanthenyl; MS: m/z=585(M+1); HPLC: Solvent B, rt=19.309.

EXAMPLE 48

$Q^5$=2-Methoxybenzyl; MS: m/z=525(M+1); Solvent B, rt=18.559.

EXAMPLE 49

$Q^5$=3,5-Dimethoxyphenyl; MS: m/z=541(M+1); Solvent B, rt=16.781.

EXAMPLES 50–58

Using a procedure similar to that described in EXAMPLE 10 except replacing 2-(isopropyloxy)phenylacetic acid with the requisite carboxylic acid, the following compounds of formula I wherein $Q^1$ is 1,4-dioxa-8-azospiro(4.5)decan-8-yl, $Q^2$ is methyl, $Q^3$ is hydrogen, $Q^4$ is dichlorophenyl, and $Q^5$ has the value defined were prepared.

EXAMPLE 50

$Q^5$3=-Isopropoxybenzyl; MS: m/z=521(M+1); HPLC: Solvent B, rt=15.175.

EXAMPLE 51

$Q^5$=2,4-Diflurobenzyl; MS: m/z=499(M+1); HPLC: Solvent B, rt=15.505.

EXAMPLE 52

$Q^5$=3-Fluorobenzyl; MS: m/z=481(M+1); HPLC: Solvent B, rt=15.278.

EXAMPLE 53

$Q^5$=2,5-Difluorobenzyl; MS: m/z=499(M+1); HPLC: Solvent B, rt=15.225.

EXAMPLE 54

$Q^5$=4-Trifluoromethylbenzyl; MS: m/z=531(M+1); HPLC: Solvent B, rt=15.805.

EXAMPLE 55

$Q^5$=3,5-Dimethylphenyl; MS: m/z=477(M+1); HPLC: Solvent B, rt=15.660.

EXAMPLE 56

$Q^5$=9-Xanthenyl; MS: m/z=553(M+1); HPLC: Solvent B, rt=15.575.

EXAMPLE 57

$Q^5$=2-Methoxybenzyl; MS: m/z=493(M+1); Solvent B, rt=15.766.

EXAMPLE 58

$Q^5$=3,5-Dimethoxyphenyl; MS: m/z=509(M+1); Solvent B, rt=14.459.

EXAMPLES 59–129

Using a procedure similar to that outlined in Scheme II and described in detail below, the following compounds of formula XI wherein $Q^5$ has the indicated value were prepared from 2-(3,4-dichlorophenyl)-2-(4-hydroxy-4-phenylpiperidino)-N-(methyl)ethylamine and the requisite carboxylic acid of formula X.

A solution of carbonyl diimide (0.3 mmol) in ethyl acetate (2 mL) was added to the requsite acid (0.3 mmol) and the mixture was stirred for 50° C. for 30 minutes. A solution of 2-(3,4-dichlorophenyl)-2-(4-hydroxy-4-phenylpiperidino)-N-(methyl)ethylamine (0.3 mmol) in ethyl acetate (5 mL) was added and the reaction tube was shaken and then stirred at 50° C. for 12 hours. The tube was allowed to cool for 30 minutes and the resulting solution was filtered. The solution was washed with saturated aqueous sodium bicarbonate (5 mL) and water (5 mL). The solvent was removed under vacuum over 2 hours. Chromatography gave the compounds of formula I, which were analysed for purity using HPLC.

For starting acids which were in the form of hydrochloride salts, an additional equivalent of triethylamine was added before addition of carbonyl diimidazole. For acids which were hydrates, an additional equivalent of carbonyl diimidazole was added.

High performance liquid chromatography was performed on a HYPERSIL ODS 5u column (purchased from Hewlet Packard, catalog number 7992402-584), at an oven temperature of 40° C. using Ultraviolet detection, at a wavelength of 280 nm. Chromatography was carried out at a flow rate of 1.5 mL/minute using the following gradient solvent system.

| Time (minutes) | Solvent C (%) | Solvent D (%) |
|---|---|---|
| 0–17 | 95 | 5 |
| 17–18 | 5 | 95 |
| 18–20 | 95 | 5 |

Solvent C triethylamine (1 mM) in water.
Solvent D triethylamine (1 mM) in acetonitrile.

EXAMPLE 59

$Q^5$=3,5-bis(trifluoromethyl)benzyl; rt=13.95.

EXAMPLE 60

$Q^5$=4-nitrobenzoyl; rt=12.7.

EXAMPLE 61

$Q^5$=9-fluorenyl; rt=13.89.

EXAMPLE 62

$Q^5$=3-adamantyl; rt=15.5.

EXAMPLE 63

$Q^5$=3,5-dimethylphenyl; rt=15.93.

EXAMPLE 64

$Q^5$=5-fluoro-3-indolyl; rt=12.64.

EXAMPLE 65

$Q^5$=2-naphthyl; rt=9.98.

EXAMPLE 66

$Q^5$=2-naphthyloxy; rt=13.52.

EXAMPLE 67

$Q^5$=β-methoxystyryl; rt=15.35.

EXAMPLE 68

$Q^5$=4-(4-methylphenylsulfonylamino)phenyl; rt=1.5.

EXAMPLE 69

$Q^5$=4-fluorobenzyl; rt=12.53.

EXAMPLE 70

$Q^5$=2-(ethoxy)ethyl; rt=12.22.

EXAMPLE 71

$Q^5$=methyl; rt=11.7.

EXAMPLE 72

$Q^5$=cyanomethyl; rt=11.57.

EXAMPLE 73

$Q^5$=methoxymethyl; rt=11.6.

EXAMPLE 74

$Q^5$=3,4,5-trimethoxystyryl; rt=12.41.

EXAMPLE 75

$Q^5$=4-(ethoxycarbonyl)butyl; rt=12.49.

EXAMPLE 76

$Q^5$=a radical of formula XII; rt=11.59.

EXAMPLE 77

$Q^5$=5-nitrofuran-2-yl; rt=12.39.
$Q^5$=5-oxo-4,5-dihydro-pyrazol-3-yl (a radical of formula XIII); rt=11.65.

EXAMPLE 79

$Q^5$=2-thienyl; rt=12.61.

EXAMPLE 80

$Q^5$=5-methoxyindol-2-yl; rt=12.76.

EXAMPLE 81

$Q^5$=pyrid-1-ylmethyl; rt=11.6.

EXAMPLE 82

$Q^5$=hydantoin-5-ylmethyl; rt=11.71.

EXAMPLE 83

$Q^5$=2-methyl-3-furyl; rt=12.42.

EXAMPLE 84

$Q^5$=a radical of formula XXIII; rt=9.95.

EXAMPLE 85

$Q^5$=4-phenoxyphenyl; rt=13.84.

EXAMPLE 86

$Q^5$=3,4-methylenedioxyphenyl; rt=12.66.

EXAMPLE 87

$Q^5$=1-benzyloxycarbonylamino-5-(tertbutoxycarbonylamino)pentanyl; rt=13.96.

EXAMPLE 88

$Q^5$=2-norbornanylmethyl; rt=13.17.

EXAMPLE 89

$Q^5$=trifluoromethyl; rt=12.93.

EXAMPLE 90

$Q^5$=2-pyrazinyl; rt=11.83.

EXAMPLE 91

$Q^5$=3-pyridyl; rt=11.83.

EXAMPLE 92

$Q^5$=phthalimidomethyl; rt=12.43.

EXAMPLE 93

$Q^5$=3-fluorophenyl; rt=12.41.

EXAMPLE 94

$Q^5$=2,4-dihydroxypyrimidin-5-yl; rt=9.7.

EXAMPLE 95

$Q^5$=3-(tertbutoxycarbonylamino)propyl; rt=12.51.

EXAMPLE 96

$Q^5$=3-pyridylmethyl; rt=11.88.

EXAMPLE 97

$Q^5$=4-pyridyl; rt=11.85.

EXAMPLE 98

$Q^5$=a radical of formula XVII; rt=10.7.

EXAMPLE 99

$Q^5$=formyl; rt=11.35.

EXAMPLE 100

$Q^5$=3-(N,N-dimethylamino)propyl; rt=11.88.

EXAMPLE 101

$Q^5$=4-fluoro-3-nitrophenyl; rt=12.07.

EXAMPLE 102

$Q^5$=4-pyridylmethyl; rt=11.84.

EXAMPLE 103

$Q^5$=styrylsulfonylmethyl; rt=12.58.

EXAMPLE 104

$Q^5$=2-nitro-3,4-dihydroxyphenyl; rt=1.62.

EXAMPLE 105

$Q^5$=fluoroacetyl; rt=11.82.

EXAMPLE 106

$Q^5$=(2-(formylamino)imidazol-4-yl)(methoxyimino)methyl; rt=12.63.

EXAMPLE 107

$Q^5$=1-acetylimino-2-imidazol-4-ylethyl; rt=10.98.

EXAMPLE 108

$Q^5$=1-acetylpiperidin-4-yl; rt=11.64.

EXAMPLE 109

$Q^5$=4-(N,N-dimethylamino)benzyl; rt=13.12.

EXAMPLE 110

$Q^5$=1-naphthylmethyl; rt=13.65.

EXAMPLE 111

$Q^5$=3,5-di(benzyloxy)phenyl; rt=15.39.

EXAMPLE 112

$Q^5$=5-(5-methyl-2-thioxoimidazolidin-4-yl)pentyl; rt=11.79.

EXAMPLE 113

$Q^5$=α-(formylamino)-α-(methyl)benzyl; rt=12.32.

EXAMPLE 114

$Q^5$=1,2,3,4-tetrahydroacridin-9-yl (a radical of formula XIX); rt=11.85.

EXAMPLE 115

$Q^5$=2-(4-methylbenzyloxy)-1-(tertbutoxycarbonylamino)ethyl; rt=13.35.

EXAMPLE 116

$Q^5$=2-benzo[b]furan-2-yl; rt=13.12.

EXAMPLE 117

$Q^5$=5,6-dimethylbenzimidazol-1-ylmethyl; rt=13.15.

EXAMPLE 118

$Q^5$=1,2,3-triazol-4-yl; rt=11.82.

EXAMPLE 119

$Q^5$=3,4-dichlorobenzyl; rt=13.6.

EXAMPLE 120

$Q^5$=4-fluorophenoxymethyl; rt=12.62.

EXAMPLE 121

$Q^5$=a radical of formula XXIV; rt=11.77.

EXAMPLE 122

$Q^5$=1-(benzyloxycarbonylaminoacetyl)pyrrolidin-3-yl; rt=13.57.

EXAMPLE 123

$Q^5$=perfluorophenyl; rt=13.55.

EXAMPLE 124

$Q^5$=tert-butoxycarbonylaminomethyl; rt=12.53.

EXAMPLE 125

$Q^5$=3,3,3-trifluoropropyl; rt=12.7.

EXAMPLE 126

$Q^5$=4-imidazolidinyl; rt=11.76.

EXAMPLE 127

$Q^5$=5-cyclohexylpentyl; rt=16.5.

EXAMPLE 128

$Q^5$=2-oxoimidazolidin-1-ylmethyl; rt=11.74.

EXAMPLE 129

$Q^5$=5-benzoylpentyl; rt=13.25.

FORMULAE

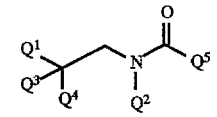

I

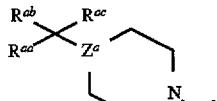

Ia

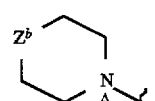

Ib

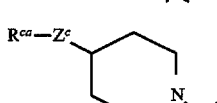

Ic

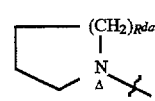

Id

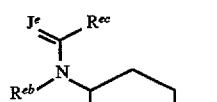

Ie

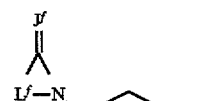

If

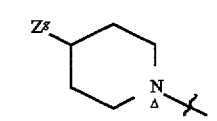

Ig

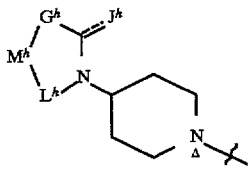

Ih

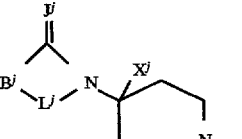

Ij

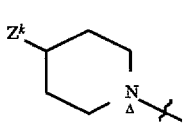

Ik

-continued
FORMULAE
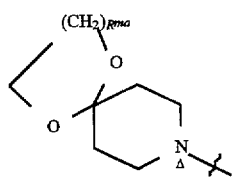 Im
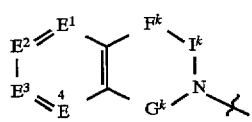 II
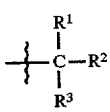 III
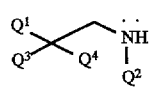 IV
 V
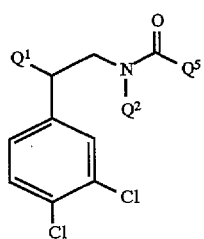 VIII
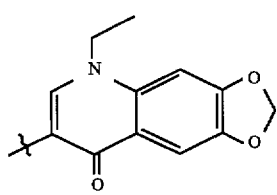 XII
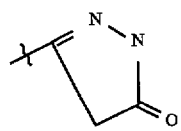 XIII
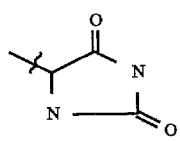 XIV
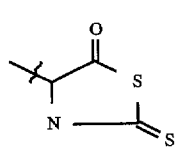 XV
-continued
FORMULAE
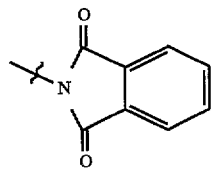 XVI
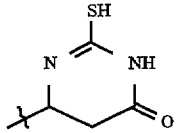 XVII
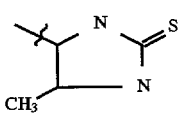 XVIII
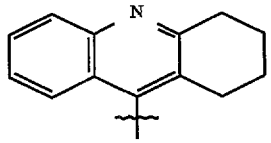 XIX
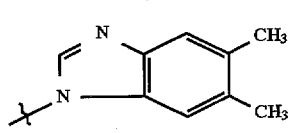 XX
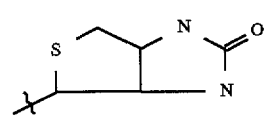 XXI
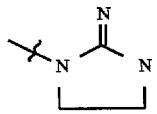 XXII
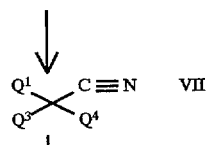 XXIII
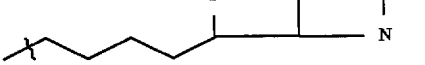 XXIV
SCHEME I
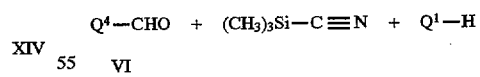

SCHEME II

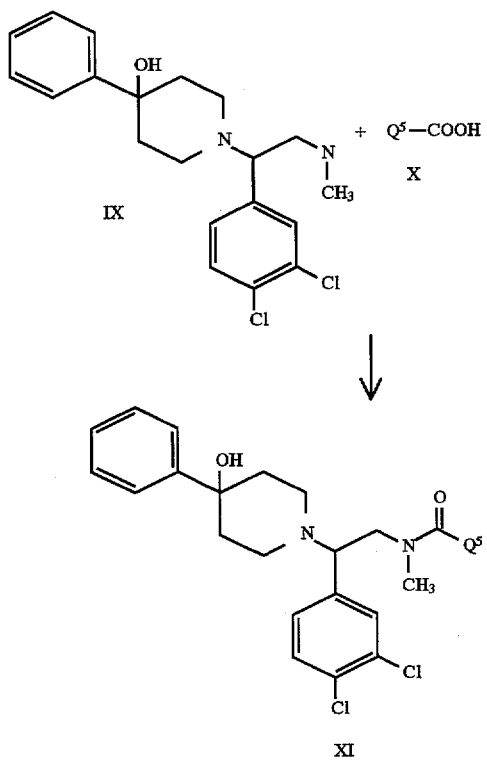

What is claimed is:

1. A compound of formula I:

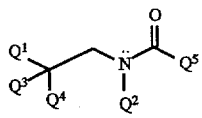

wherein $Q^1$ is selected from radicals of formulae Ic, If, Ib, Ij, and Ik,

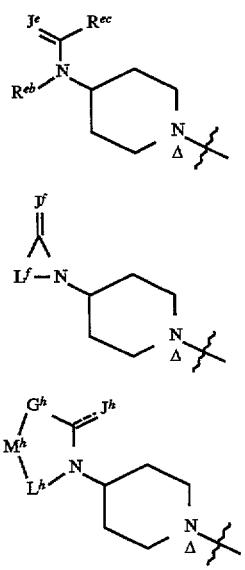

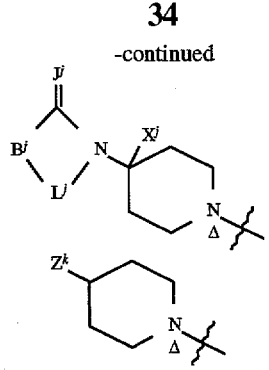

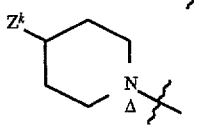

for a radical of formula Ie, $J^e$ is oxygen, sulfur or $NR^{ea}$ in which $R^{ea}$ is hydrogen or (1–3C)alkyl; $R^{eb}$ is hydrogen, (1–6C)alkyl which may bear a hydroxy substituent and/or one to three fluoro substituents, (3–6C)alkenyl (in which a vinyl carbon is not bound to nitrogen), 2-hydroxyethyl, (3–7C)cycloalkyl, Ar or Het; $R^{ec}$ is hydrogen, (1–6C)alkyl which may bear a hydroxy substituent and/or one to three fluoro substituents, (3–6C)cycloalkyl, (1–5C)alkoxy (only when $J^e$ is oxygen), (3–6C)cycloalkoxy (only when $J^e$ is oxygen), or an amino group of formula $NR^{ed}R^{ee}$ containing zero to seven carbon atoms in which each of $R^{ed}$ and $R^{ee}$ is independently hydrogen, (1–5C)alkyl or (3–6C)cycloalkyl, or the radical $NR^{ed}R^{ee}$ is pyrrolidino, piperidino, morpholino, thiomorpholino (or its S-oxide) or piperazinyl (which piperazinyl group may hear a (1–3C)alkyl substituent at the 4-position);

for a radical of formula If, $J^f$ is oxygen, sulfur or $NR^{fa}$ in which $R^{fa}$ is hydrogen or (1–3C)alkyl; $L^f$ is a divalent hydrocarbon group in which the 1-position is bound to the carbon bearing the group $J^f$, the divalent group $L^f$ being selected from trimethylene, cis-propenylene, tetramethylene, cis-butenylene, cis-but-3-enylene, cis, cis-butadienylene, pentamethylene and cis-pentenylene which divalent group $L^f$ itself may bear one or two methyl substituents;

for a radical of formula Ih, $G^h$ denotes a single bond, a double bond or a divalent hydrocarbon radical; $J^h$ denotes a radical joined to the ring by a single bond if $G^h$ denotes a double bond or, otherwise, a radical joined by a double bond; $M^h$ denotes a heteroatom, a substituted heteroatom, or a single bond; and $L^h$ denotes a hydrocarbon radical in which the 1-position is attached to $M^h$; wherein the values of $G^h$, $J^h$, $M^h$ and $L^h$ are selected from (a) $G^h$ is a single bond; $J^h$ is oxo or thioxo; $M^h$ is oxy, thio or $NR^{ha}$; and $L^h$ is $L^{ha}$;

(b) $G^h$ is a single bond; $J^h$ is $NR^{hb}$; $M^h$ is $NR^{ha}$; and $L^h$ is $L^{ha}$;

(c) $G^h$ is a double bond, $J^h$ is $OR^{ha}$, $SR^{ha}$ or $NR^{hc}R^{hd}$, $M^h$ is nitrogen; and $L^h$ is $L^{ha}$;

(d) $G^h$ is methylene which may hear one or two methyl substituent; $J^h$ is oxo, thioxo or $NR^{hc}$; $M^h$ is oxy, thio, sulfinyl, sulfonyl or $NR^{ha}$; and $L^h$ is $L^{hb}$;

(e) $G^h$ is a single bond; $J^h$ is oxo, thioxo or $NR^{he}$; $M^h$ is nitrogen; and $L^h$ is $L^{hc}$;

(f) $G^h$ is methine, which may bear a (1–3C)alkyl substituent; $J^h$ is oxo. thioxo or $NR^{hc}$; $M^h$ is nitrogen; and $L^h$ is $L^{hd}$;

(g) $G^h$ is cis-vinylene, which may bear one or two methyl substituents; $J^h$ is oxo, thioxo, or $NR^{hc}$; $M^h$ is nitrogen; and $L^h$ is $L^{he}$; and (h) $G^h$ is a single bond; $J^h$ is oxo or thioxo; $M^h$ is a single bond; and $L^h$ is $L^{hf}$; wherein $R^{ha}$ is hydrogen or (1–3C)alkyl; $R^{hb}$ is hydrogen, (1–3C) alkyl, cyano, (1–3C)alkylsulfonyl or nitro; $R^{hc}$ and $R^{hd}$ are independently hydrogen or (1–3C)alkyl or the radical $NR^{hc}R^{hd}$ is pyrrolidino, piperidino, morpholino, thiomorpholino for its S-oxide) or piperazinyl (which piperazinyl may bear a (1–3C)alkyl substituent at the 4-position); $R^{he}$ is hydrogen or (1–3C)alkyl; $L^{ha}$ is ethylene, cis-vinylene, trimethylene or tetramethylene which radical $L^{ha}$ itself may bear one or two methyl substituents; $L^{hb}$ is ethylene or trimethylene which radical $L^{hb}$ itself may bear one or two methyl substituents; $L^{hc}$ is prop-2-en-1-yliden-3-yl, which radical $L^{hc}$ itself may bear one or two methyl substituents; $L^{hd}$ is cis-vinylene, which radical $L^{hd}$ itself may hear one or two methyl substituents; $L^{he}$ is methine, which radical $L^{he}$ itself may bear a (1–3C)alkyl substituent; and $L^{hf}$ is 4-oxabutan-1,4-diyl;

for a radical of formula Ij, $X^j$ is (1–6C)alkyl, —$CH_2OR^{ja}$, —$CH_2SR^{ja}$, —$CH_2S(O)R^{jg}$, —$CH_2S(O)_2R^{jg}$, —$COR^{ja}$, —$COOR^{ja}$, —$C(=J^{ja})NR^{ja}R^{jc}$, —$C(R^{ja})(OR^{jd})(OR^{jc})$, —$CH_2N(R^{ja})C(=J^{ja})R^{jf}$, —$CH_2N(R^{ja})COOR^{jg}$ or —$CH_2N(R^{ja})C(=J^{ja})NR^{jb}R^{jc}$, $B^j$ is a direct bond and $L^j$ is a hydrocarbon chain in which the 1-position is bound to $B^j$ and $L^j$ is selected from trimethylene, tetramethylene, cis-1-butenylene and cis, cis-butadienylene; or $B^j$ is $N(R^{jh})$ and $L^j$ is a hydrocarbon chain selected from ethylene, trimethylene and cis-vinylene; $B^j$ is N and $L^j$ is a hydrocarbon chain in which the 1-position is bound to $B^j$ and $L^j$ is cis,cis-prop-2-en-1-ylidin-3-yl; $J^j$ and $J^{ja}$ are independently oxygen or sulfur; $R^{ja}$, $R^{jf}$ and $R^{jh}$ are independently hydrogen or (1–6C)alkyl; $R^{jb}$ and $R^{jc}$ are independently hydrogen or (1–6C)alkyl; or the radical $NR^{jb}R^{jc}$ is pyrrolidino, piperidino, morpholino, thiomorpholino (or its S-oxide) or piperazinyl independently (1–3C) alkyl (which piperazinyl may bear a (1–3C)alkyl substituent at the 4-position); $R^{jd}$ and $R^{je}$ are independently (1–3C)alkyl; or together form a divalent hydrocarbon chain selected from ethylene and trimethylene; $R^{jg}$ is (1–6C)alkyl;

for a radical of formula Ik, $Z^k$ is a nitrogen linked radical of formula II:

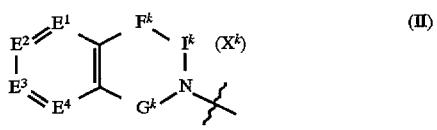

wherein $E^1$, $E^2$, $E^3$ and $E^4$ form a divalent four membered chain (—$E^1=E^2—E^3=E^4$—) in which each of $E^1$, $E^2$, $E^3$ and $E^4$ a is a methine; or in which one or two of $E^1$, $E^2$, $E^3$ and $E^4$ is nitrogen and the remaining $E^1$, $E^2$, $E^3$ and $E^4$ are methine; and further wherein one or more of $E^1$, $E^2$, $E^3$ and $E^4$ which is methine may bear a halo, (1–3C)alkyl, hydroxy, (1–3C)alkoxy, (1–3C) alkylthio, (1–3C)alkylsulfinyl or (1–3C)alkylsulfonyl substituent; and wherein the radicals $F^k$ $G^k$, and $I^k(X^k)$ are selected from (a) $G^k$ is a direct bond, $I^k(X^k)$ is a radical having the formula =$C(Z^k)$— and $F^k$ is a radical selected from —CH= and —N=;

(b) $G^k$ is a direct bond, $I^k(X^k)$ is a radical having the formula —$C(=J^k)$— and $F^k$ is a radical selected from —$N(R^{kf})$—, —$CH_2$—$CH_2$—, —CH=CH—, —$CH_2$—$N(R^{kf})$— and —CH=N—;

(c) $G^k$ is a radical having the formula —$CH_2$—, $I^k(X^k)$ is a radical having formula —$C(=J^k)$— and $F^k$ is selected from —$CH_2$— and —$N(R^{kf})$—; and (d) $G^k$ is selected from —$CH_2$—, —$CH_2$—$CH_2$—, —CH=CH— and —N=CH—, $I^k(X^k)$ is a radical having the formula —$C(=J^k)$— and $F^k$ is a direct bond; wherein $J^k$ is oxygen or sulfur; $Z^k$ is —$OR^{ka}$, —$SR^{ka}$, —$COR^{ka}$, —$COOR^{ka}$, —$C(=J^{ka})NR^{kb}R^{kc}$ or —$C(R^{ka})(OR^{kd})$ ($OR^{ke}$); $J^{ka}$ is oxygen or sulfur; $R^{ka}$ and $R^{kf}$ are independently hydrogen or (1–6C)alkyl; $R^{kb}$ and $R^{kc}$ are independently hydrogen or (1–6C)alkyl; or the radical $NR^{kb}R^{kc}$ is pyrrolidino, piperidino, morpholino, thiomorpholino (or its S-oxide) or piperazinyl (which piperazinyl may bear a (1–3C)alkyl substituent at the 4-position); $R^{kd}$ and $R^{ke}$ are independently (1–3C)alkyl or $R^{kd}$ and $R^{ke}$ together form ethylene or trimethylene; or $Z^k$ is an imido radical selected from phthalimido, succinimido, maleimido, glutarimido, and 3-oxa-, 3-thio- and 3-azaglutarimido, in which the imido radical may bear one or more (1–3C)alkyl substituents and, in addition, the aromatic portion of the phthalimido may bear one or more halo, hydroxy or (1–3C)alkoxy substituents;

for a radical $Q^1$, Ar is a phenyl radical or an ortho-fused bicyclic carbocyclic radical of nine of ten ring atoms in which at least one ring is aromatic, which radical Ar may be unsubstituted or may bear one or more substituents selected from halo, cyano, trifluoromethyl, (1–4C)alkyl, (14C)alkoxy, methylenedioxy, hydroxy, mercapto, —$S(O)_nR^{xa}$, (1–5C)alkanoyl, (1–5C) alkanoyloxy, nitro, $NR^{xb}R^{xc}$, $NR^{xd}R^{xe}$, $C(=NR^{xf})NR^{xg}R^{xh}$, $CONR^{xb}R^{xc}$ and $COOR^{xj}$ wherein n is the integer 0, 1, or 2; $R^{xa}$ is (1–6C)alkyl, (3–6C)cycloalkyl or phenyl (which phenyl may bear a halo, trifluoromethyl, (1–3C)alkyl or (1–3C)alkoxy substitutent); the radical $NR^{xb}R^{xc}$ contains zero to seven carbons and each or $R^{xb}$ and $R^{xc}$ is independently hydrogen, (1–5C)alkyl or (3–6C)cycloalkyl, or the radical $NR^{xb}R^{xc}$ is pyrrolidino, piperidino, morpholino, thiomorpholine (or its S-oxide) or piperazinyl (which piperazinyl may bear a (1–3C)alkyl substituent at the 4-position); and wherein $R^{xd}$ is hydrogen or (1–4C) alkyl and $R^{xc}$ is (1–5C)alkanoyl, benzoyl; or a group of formula $C(=J^x)NR^{xg}R^{xh}$ in which $J^x$ is oxygen, sulfur, $NR^{xf}$ or $CHR^{xi}$; $R^{xf}$ is hydrogen, (1–5C)alkyl or together with $R^{xg}$ forms an ethylene or trimethylene diradical, the radical $NR^{xg}R^{xh}$ contains zero to 7 carbons and each of $R^{xg}$ and $R^{xb}$ is independently hydrogen, (1–5C)alkyl or (3–6C)cycloalkyl, or the radical $NR^{xg}R^{xh}$ is pyrrolidino, piperidino, morpholino, thiomorpholino (or its S-oxide) or piperazinyl (which piperazinyl may bear a (1–3C)alkyl substituent at the 4-position); or $R^{xg}$ together with $R^{xf}$ forms an ethylene or trimethylene diradical and $R^{xh}$ is hydrogen or (1–5C) alkyl; $R^{xi}$ is cyano, nitro, (1–5C)alkylsulfonyl or phenylsulfonyl; and $R^{xj}$ is hydrogen, (1–5C)alkyl or benzyl; and Het is a radical (or stable N-oxide thereof) attached via a ring carbon of a monocyclic aromatic ring containing five or six ring atoms consisting of carbon and one to four heteroatoms selected from oxygen, sulfur and nitrogen, or an ortho-fused bicyclic heterocycle derived therefrom by fusing a propenylene, trimethylene, tetramethylene or benz-diradical, which radical Het may be unsubstituted or may be substituted on carbon by one or more of the substituent defined above for Ar and may be substituted on nitrogen by (1–3C)alkyl;

$Q^2$ and $Q^3$ are independently hydrogen or (1–3C)alkyl;

$Q^4$ is phenyl which may bear one or two substituents independently selected from halo, trifluoromethyl, hydroxy, (1-3C)alkoxy, (1-3C)alkyl and methylenedioxy; or $Q^4$ is thienyl, imidazolyl, benzo[b]thiophenyl or naphthyl any of which may bear a halo substituent; or $Q^4$ is biphenylyl; or $Q^4$ is carbon-linked indolyl which may bear a benzyl substituent at the 1-position; and $Q^5$ is formyl, 4-imidazolidinyl, 3-pyrrolidinyl (wherein the nitrogen may optionally be substituted by a substituent selected from (1-3C)alkyl, acyl, and benzyloxycarbonylaminoacetyl), (3-6C)cycloalkyl, trifluoromethyl, 4-piperidino (wherein the nitrogen may optionally be substituted by a substituent selected from (1-3C)alkyl, and acyl), aryl, heteroaryl, pyrid-1-ylmethyl, fluorenyl, b-styryl, a radical of formula XII–XXII:

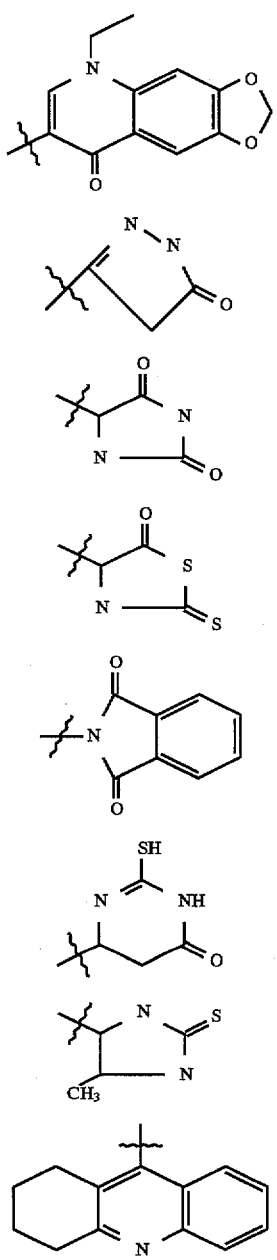

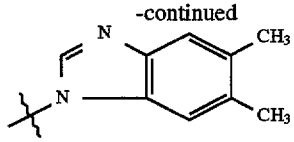

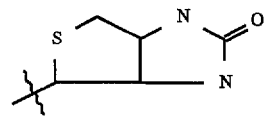

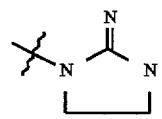

or xanthenyl; or $Q^5$ is (1-8C)alkyl which may be substituted by 0–3 substituents selected from aryl, heteroaryl, (aryl)oxy, aryl(1-3C)-alkyl, heteroaryl (1-3C)alkyl, (1-6C)alkyl, (heteroaryl)oxy, benzyloxy. (3-6C)cycloalkyl, adamantyl, norbornanyl, b-styryl, cyano, trifluoromethyl, oxo, hydroxy), (1-4C)alkoxy, $-NR^aR^b$, $-NC(=O)NR^cR^d$, $-NC(=O)OR^e$, $-C(=O)OR^f$, $-S(O)R^g$, $-S(O)_2R^h$, $=NR^i$, $SR^j$, and the radicals of formulae XII–XXII;

$R^a$–$R^b$ are independently selected from hydrogen, acyl, formyl, and (1-4C)alkyl, or the group $NR^aR^b$ may form a cyclic group selected from pyrrolidino, piperidino, morpholino, thiomorpholino (or its S-oxide) or piperazinyl (which piperazinyl may bear a (1-3C)alkyl substituent at the 4-position);

$R^c$–$R^f$ and $R^j$ are independently selected from hydrogen, phenyl, benzyl, phenethyl and (14C)alkyl;

$R^g$ and $R^h$ are independently selected from hydrogen, phenyl, benzyl, phenethyl, b-styryl and (14C)alkyl;

$R^i$ is hydrogen, (1-4C)alkyl, acyl or (1-4C)alkoxy;

wherein any aryl or heteroaryl in, or any aryl or heteroaryl portion of, $Q^5$, or any aryl or heteroaryl portion of $R^a$–$R^j$, may be unsubstituted or may bear 1–5 substituents selected from halo, cyano, trifluoromethyl, (1-4C) alkyl, (1-4C)alkoxy, methylenedioxy, phenoxy, benzyloxy, $NR^kR^m$, $-NS(O)_2$aryl (wherein the aryl group may be substituted by 0–3 (1-3C)alkyl groups), hydroxy, $-SR^n$, and nitro; and wherein any b-styryl may optionally be substituted at the b-position by a substituent selected from (1-3C)alkoxy;

wherein $R^k$–$R^m$ are independently selected from hydrogen, acyl, formyl, and (1-4C)alkyl, or the group $NR^kR^m$ may form a cyclic group selected from pyrrolidino, piperidino, morpholino, thiomorpholino (or its S-oxide) or piperazinyl (which piperazinyl may bear a (1-3C)alkyl substituent at the 4-position); and $R^n$ is hydrogen or (1-3C)alkyl;

or the N-oxide of a piperidino nitrogen in $Q^1$ indicated by A;

or a pharmaceutically acceptable salt thereof;

or a quaternary ammonium salt thereof in which the piperidino nitrogen in $Q^1$ indicated by A is a quadricovalent ammonium nitrogen wherein the fourth radical on the nitrogen $R^1$ is (1-4C)alkyl or benzyl and the associated counterion A is a pharmaceutically acceptable anion.

2. A compound of formula I:

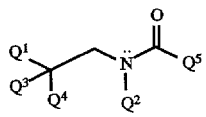

wherein
Q¹ is 4-hydroxy-4-phenylpiperidino, 4-acetamido-4-phenylpiperidino, 4-(2-methylsulfinylphenyl) piperidino, or 4-(2-oxoperhydropyrimidin-1-yl) piperidino; Q² is methyl, ethyl or propyl; $Q^{3'}$ is hydrogen; Q⁴ is 3,4-dichlorophenyl or 3,4-methylenedioxyphenyl; and Q⁵ is phenyl, benzyl, 2-methoxyphenyl, 3,5-bis(trifluoromethyl)benzyl, 2-isopropoxybenzyl or 3,5-bis(trifluoromethyl)phenyl; or a pharmaceutically acceptable salt thereof.

3. A compound of Formula VIII

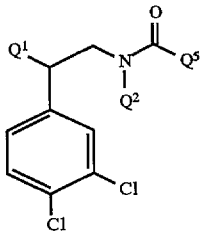

wherein, Q¹ is 4-hydroxy-4-phenylpiperidino, 4-acetamido-4-phenylpiperidino, or 4-(2-oxoperhydropyrimidin-1-yl) piperidino; Q² is (1–3C)alkyl; and Q⁵ is phenyl, benzyl, 2-methoxyphenyl, 2-methoxybenzyl, 3,5-bis(trifluoromethyl)phenyl, 3,5-bis(trifluoromethyl)benzyl, 3,5-dimethylphenyl, 3,5-dimethylbenzyl, 3,5-dichlorophenyl, 3,5-dichlorobenzyl, 3,5-dimethoxyphenyl, or 3,5-dimethoxybenzyl;

or the N-oxide of the piperidino nitrogen in Q¹;

or a pharmaceutically acceptable salt thereof;

or a quaternary ammonium salt thereof in which the piperidino nitrogen in Q¹ is a quadricovalent ammonium nitrogen wherein the fourth radical on the nitrogen R¹ is (1–4C)alkyl or benzyl and the associated counterion A is a pharmaceutically acceptable anion.

4. A compound as claimed in claim 3 wherein, Q¹ is 4-hydroxy-4-phenylpiperidino; Q² is (1–3C)alkyl; and Q⁵ is phenyl, benzyl, 2-methoxyphenyl, 3,5-bis(trifluoromethyl) benzyl, 2-isopropoxybenzyl or 3,5-bis(trifluoromethyl) phenyl.

5. A compound as claimed in claim 3 wherein, Q¹ is 4-hydroxy-4-phenylpiperidino; Q² is (1–3C)alkyl; and Q⁵ is phenyl, benzyl, 2-methoxyphenyl, 3,5-bis(trifluoromethyl) benzyl, 2-isopropoxybenzyl or 3,5-bis(trifluoromethyl) phenyl.

* * * * *